(12) United States Patent
Kil et al.

(10) Patent No.: US 7,546,157 B1
(45) Date of Patent: Jun. 9, 2009

(54) SYSTEM AND METHOD FOR EMULATING A SURFACE EKG USING INTERNAL CARDIAC SIGNALS SENSED BY AN IMPLANTABLE MEDICAL DEVICE

(75) Inventors: Jong Kil, Glendale, CA (US); Gene A. Bornzin, Simi Valley, CA (US); Peter Boileau, Valencia, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 441 days.

(21) Appl. No.: 10/735,948

(22) Filed: Dec. 12, 2003

(51) Int. Cl.
  *A61B 5/04* (2006.01)
(52) U.S. Cl. .................................... 600/510
(58) Field of Classification Search ............ 600/30, 600/510, 509; 607/5, 9, 27–28
  See application file for complete search history.

(56) References Cited

U.S. PATENT DOCUMENTS

| | | | |
|---|---|---|---|
| 5,193,550 A * | 3/1993 | Duffin ........................ | 600/510 |
| 5,265,602 A | 11/1993 | Anderson et al. ............. | 607/9 |
| 5,324,310 A | 6/1994 | Greeninger et al. ........... | 607/28 |
| 5,620,466 A | 4/1997 | Haefner et al. | |
| 5,658,317 A | 8/1997 | Haefner et al. | |
| 5,740,811 A | 4/1998 | Hedberg et al. ............. | 128/697 |
| 6,091,990 A | 7/2000 | Hsu et al. | |
| 6,169,918 B1 | 1/2001 | Haefner et al. | |
| 6,249,705 B1 | 6/2001 | Snell | |
| 6,253,102 B1 | 6/2001 | Hsu et al. | |
| 6,266,566 B1 | 7/2001 | Nichols et al. | |
| 6,501,983 B1 | 12/2002 | Natarajan et al. | |
| 6,622,045 B2 | 9/2003 | Snell | |
| 6,633,776 B2 | 10/2003 | Levine et al. | |
| 6,658,283 B1 | 12/2003 | Bornzin et al. | |

(Continued)

FOREIGN PATENT DOCUMENTS

EP   0784996   7/1997

OTHER PUBLICATIONS

S. Serge Barold et al., "The Paced 12-Lead Electrocardiogram Should No Longer Be Neglected in Pacemaker Follow-Up," PACE, vol. 24 (Oct. 2001); pp. 1455-1458.

(Continued)

*Primary Examiner*—George R Evanisko
*Assistant Examiner*—Rex Holmes

(57) ABSTRACT

A surface electrocardiogram (EKG) is emulated using signals detected by the internal leads of an implanted device. In one example, the emulation is performed using a technique that concatenates portions of signals sensed using different electrodes, such as by combining far-field ventricular signals sensed in the atria with far-field atrial signals sensed in the ventricles or by combining near-field signals sensed in the atria with near-field signals sensed in the ventricles. In another example, the emulation is performed using a technique that selectively amplifies or attenuates portions of a single signal sensed using a single pair of electrodes, such as by attenuating near-field portions of an atrial unipolar signal relative to far-field portions of the same signal or by attenuating atrial portions of a cross-chamber signal relative to ventricular portions to the same signal. The surface EKG emulation may be performed by the implanted device itself or by an external programmer based on cardiac signals transmitted thereto.

10 Claims, 20 Drawing Sheets

U.S. PATENT DOCUMENTS

| | | | |
|---|---|---|---|
| 6,714,819 B1 | 3/2004 | Sloman | |
| 6,748,274 B2 | 6/2004 | Levine et al. | |
| 6,813,514 B1 * | 11/2004 | Kroll et al. | 600/509 |
| 2002/0123770 A1 | 9/2002 | Combs et al. | |

OTHER PUBLICATIONS

NonFinal Office Action, mailed Jul. 20, 2005: Related U.S. Appl. No. 10/736,111.
NonFinal Office Action, mailed Nov. 1, 2005: Related U.S. Appl. No. 10/736,111.
NonFinal Office Action, mailed May 3, 2006: Related U.S. Appl. No. 11/736,111.
Final Office Action, mailed Aug. 25, 2006: Related U.S. Appl. No. 10/736,111.
Advisory Action, mailed Oct. 12, 2006: Related U.S. Appl. No. 10/736,111.
NonFinal Office Action, mailed Nov. 27, 2006: Related U.S. Appl. No. 10/736,111.
Final Office Action, mailed Jul. 16, 2007: Related U.S. Appl. No. 10/736,111.
NonFinal Office Action, mailed Jul. 1, 2005: Related U.S. Appl. No. 10/735,944.
NonFinal Office Action, mailed Nov. 1, 2005: Related U.S. Appl. No. 10/735,944.
NonFinal Office Action, mailed May 3, 2006: Related U.S. Appl. No. 10/735,944.
Final Office Action, mailed Aug. 25, 2006: Related U.S. Appl. No. 10/735,944.
Advisory Action, mailed Oct. 12, 2006: Related U.S. Appl. No. 10/735,944.
NonFinal Office Action, mailed Nov. 27, 2006: Related U.S. Appl. No. 10/735,944.
Final Office Action, mailed Jul. 16, 2007: Related U.S. Appl. No. 10/735,944.
Notice of Allowance, mailed Sep. 21, 2007: Related U.S. Appl. No. 10/735,944.
Notice of Allowance, mailed Sep. 28, 2007: Related U.S. Appl. No. 10/736,111.
Notice of Allowance, mailed Nov. 2, 2007: Related U.S. Appl. No. 10/736,111.
Notice of Allowance, mailed Nov. 1, 2007: Related U.S. Appl. No. 10/735,944.
NonFinal Office Action, mailed Jun. 27, 2008: Related U.S. Appl. No. 11/432,636.
NonFinal Office Action, mailed Apr. 17, 2008: Related U.S. Appl. No. 11/213,454.
NonFinal Office Action, mailed Jun. 20, 2008: Related U.S. Appl. No. 11/431,955.
NonFinal Office Action, mailed Mar. 27, 2008: Related U.S. Appl. No. 11/030,380.
Final Office Action, mailed Nov. 28, 2008: Related U.S. Appl. No. 11/030,380.
Final Office Action, mailed Dec. 24, 2008: Related U.S. Appl. No. 11/213,454.
Final Office Action, mailed Dec. 19, 2008: Related U.S. Appl. No. 11/432,636.
Final Office Action, mailed Dec. 19, 2008: Related U.S. Appl. No. 11/431,955.

* cited by examiner

PRIOR ART    COMBINED SURFACE EKG

SYSTEM AND METHOD FOR EMULATING A SURFACE EKG USING INTERNAL CARDIAC SIGNALS SENSED BY AN IMPLANTABLE MEDICAL DEVICE

CROSS-REFERENCE TO RELATED APPLICATIONS

This application is related to copending U.S. patent applications: 1) Ser. No. 10/736,111, titled "System and Method for Emulating a Surface EKG Using Internal Cardiac Signals Sensed by an Implantable Medical Device"; and 2) Ser. No. 10/735,944, titled "System and Method for Emulating a Surface EKG Using Internal Cardiac Signals Sensed by an Implantable Medical Device"; all applications filed concurrently herewith.

FIELD OF THE INVENTION

The invention generally relates to implantable medical devices, such as pacemakers or implantable cardioverter-defibrillators ("ICDs"), and to external programmers for use therewith and, in particular, to techniques for emulating a surface electrocardiogram (EKG) using internal electrical cardiac signals.

BACKGROUND

A pacemaker is an implantable medical device that recognizes various arrhythmias such as an abnormally slow heart rate (bradycardia) or an abnormally fast heart rate (tachycardia) and delivers electrical pacing pulses to the heart in an effort to remedy the arrhythmias. An ICD is an implantable device that additionally recognizes atrial fibrillation (AF) or ventricular fibrillation (VF) and delivers electrical shocks to terminate fibrillation. Pacemakers and ICDs detect arrhythmias by sensing internal electrical cardiac signals using leads implanted within the heart. The internal signals comprise an intracardiac electrogram (IEGM). Within the IEGM, the normal contraction of atrial heart muscle tissue appears as a P-wave whereas the normal contraction of ventricular muscle tissue appears as an R-wave (sometimes referred to as the "QRS complex"). More specifically, the P-wave corresponds to the electrical depolarization of atrial tissue and the R-wave corresponds to the depolarization of ventricular tissue. The subsequent electrical repolarization of the ventricular tissue appears within the IEGM as a T-wave. Strictly speaking, P-waves, R-waves and T-waves are features of a surface electrocardiogram (EKG or ECG). For convenience, the terms P-wave, R-wave and T-wave are also used herein to refer to the corresponding internal signal component.

Pacemakers and ICDs are often configured to be used in conjunction with a programmer that allows a physician to program the operation of the implanted device to, for example, control the specific parameters by which the device detects arrhythmia and responds thereto. For example, the programmer may allow the physician to specify the sensitivity with which the implanted device senses electrical signals within the heart and to further specify the amount of electrical energy to be employed for pacing the heart. Additionally, the programmer may be configured to receive and display a wide variety of diagnostic information detected by the implanted device, such as graphs of the IEGM. In addition, the programmer may operate to analyze data received from the device to assist the physician in rendering diagnoses as to possible arrhythmias and to then assist the physician in programming the device to provide appropriate therapy.

Current state of the art implantable cardiac stimulation devices may have dozens or hundreds of programmable parameters that can be individually programmed using the external programmer. The programmable parameters permit the operation of the cardiac stimulation device to be tailored to the needs of the particular patient to provide optimal therapy while minimizing the risk of any unnecessary therapy. Unfortunately, it is often difficult to predict the effect within a given patient to a selected set of parameter settings. Hence, a potentially viable set of parameters is chosen by the physician, the implantable cardiac stimulation device is programmed using the selected set of parameters and then the patient is sent home. Weeks or months later the patient returns to the physician's office for a follow-up appointment so that they physician may evaluate the effect of the selected parameters. Typically, the follow-up evaluation consists of the physician making judgments based upon a review of diagnostic information provided by the implanted device (including the IEGM) in combination with a surface EKG provided by a separate surface EKG unit. As part of the review, the physician may also compare new surface EKGs with recorded surface EKGs from previous sessions. In any case, the physician adjusts the programming parameters of the implanted device to improve therapy delivered to the patient. Again, the patient is sent home for several more weeks or months until another follow-up visit. This cycle may be repeated numerous times before optimal device settings are determined by the physician.

To obtain a surface EKG, typically, ten electrodes are manually attached the skin of the patient in the configuration shown in FIG. 1. The surface EKG derived from the ten electrodes is referred to as a "12-lead" EKG because twelve signals are derived from the ten electrodes—including signals from each of the individual electrodes plus signals between certain pairs of electrodes. More specifically, the ten electrodes include four limb electrodes and six "chest" electrodes. The chest electrodes are labeled: $V_1$-$V_6$. The limb electrodes are: RA (right arm), LA (left arm), LL (left leg) and right leg (RL), the last of which is optional. The chest electrodes provide one signal per electrode, referred to as the $V_1$-$V_6$ signals. The RA, LA and LL limb electrodes also provide one signal per electrode, referred to as the aVR, aVL and aVF signals (with F signifying foot as opposed to leg.) Finally, the difference between each pairing of the RA, LA and LL limb electrodes is considered a separate "lead" (referred to as the Einthoven leads I, II and III) and hence provide the last three signals of the surface EKG. The twelve signals of the surface EKG are summarized in TABLE I, along with the electrodes from which the signals are derived.

TABLE I

| PHYSICAL LEADS | SURFACE EKG SIGNALS |
| --- | --- |
| $V_1$ | $V_1$ |
| $V_2$ | $V_2$ |
| $V_3$ | $V_3$ |
| $V_4$ | $V_4$ |
| $V_5$ | $V_5$ |
| $V_6$ | $V_6$ |
| LA-RA | I |
| LL-RA | II |
| LL-LA | III |
| RA | aVR |
| LA | aVL |
| LL | Avf |

The twelve signals are combined to yield a single surface EKG, an example of which is shown in FIG. 2. It is particularly important for the physician to review the surface EKG during follow-up programming sessions. See: "The Paced Electrocardiogram Should No Longer Be Neglected in Pacemaker Follow-Up", by S. Serge Barold; Paul A. Levine; I. Eli Ovsyshcher, PACE 2001; 24: 1455-1458. However, the need to manually attach and remove each of the surface EKG electrodes from the patient during each follow-up session is a burden to the physician (or his or her staff) and a considerable inconvenience to the patient. In many cases, the skin of the patient must be shaved and sanded in the locations where the electrodes are to be attached to provide adequate electrical conduction. This can be quite uncomfortable and, in some cases, embarrassing for the patient. Moreover, the time required to attach and then remove the electrodes adds to the overall cost of the follow-up session. Also, from one follow-up session and another, the electrodes may not be placed at the exact same locations on the patient, thus resulting in somewhat different surface EKGs and making it more difficult for the physician to properly identify actual differences in cardiac signals of the patient from one session to the next.

As can be appreciated, it would be desirable to eliminate the need for attaching the electrodes of the surface EKG to patients during follow-up sessions to thereby reduce the cost and inconvenience to the patient and to eliminate problems resulting from differing electrode placement. One proposed solution is to emulate the surface EKG using internal electrical cardiac signals sensed by the implanted device so that, during a follow-up session, a separate surface EKG system is not required and external electrodes need not be attached to the patient. One effective technique for emulating a surface EKG using internal electrical signals is described in U.S. patent application Ser. No. 10/334,741 to Kroll et al., entitled "System and Method for Emulating a Surface EKG Using Implantable Cardiac Stimulation Device", filed Dec. 30, 2002, which is assigned to the assignee of the present application and is incorporated by reference herein. With the technique of Kroll et al., each of the separate signals of the 12-lead EKG are individually emulated based on IEGM signals derived from implanted electrodes.

Although Kroll et al. provides a powerful technique for emulating all twelve signals of the EKG, in many cases, it is not always necessary for the physician to separately review the individual signals and only a combined surface EKG is needed. Hence, rather than separately emulating individual 12-lead EKG signals and then combining the signals into single surface EKG, it would instead be desirable to provide simpler and more direct techniques for emulating a combined surface EKG.

It should be noted that there are some existing techniques that serve to directly emulate a single combined surface EKG. See, for example, U.S. Pat. No. 5,740,811 to Hedberg et al., entitled "Device and Method for Generating a Synthesized ECG". With the technique of Hedberg et al., a neural network is employed to convert electrical signals derived from implanted electrodes into a single emulated or "synthesized" surface EKG. Although the technique of Hedberg et al. directly emulates a single combined surface EKG, it appears to be computationally intensive. Accordingly, it would be desirable to provide improved techniques for emulating a single combined surface EKG that are not computationally intensive.

SUMMARY

In accordance with a first general aspect, techniques are provided for emulating a surface EKG of a patient in which an implantable cardiac stimulation device is implanted by using a concatenation-based technique wherein portions of separate internal cardiac signals are selectively combined to yield an emulated EKG. Briefly, at least two separate cardiac signals are sensed using electrodes implanted within the patient and then portions of the separate cardiac signals are selectively concatenated to yield the emulated surface EKG. For example, selected portions of an atrial channel unipolar signal may be concatenated with selected portions of a ventricular channel unipolar signal so as to yield the emulated surface EKG. By generating the emulated surface EKG by concatenating portions of internal cardiac signals, a reasonably accurate emulation may be achieved without requiring computationally-intensive techniques, thereby consuming fewer resources than more intensive techniques and permitting real-time emulation to be more easily achieved. Herein, the term "emulation" as applied to the surface EKG refers to the generation of a suitable surrogate, substitute or proxy for an actual surface EKG. The use of the term is not intended to imply that an exact or closely similar copy of the surface EKG necessarily be generated. Rather, it is typically sufficient that the emulated surface EKG be sufficiently similar to the actual surface EKG to aid the physician during a follow-up programming session. In other words, the emulated EKG provides for generating a suitable "visualization" of the actual surface EKG.

In one particular example, far-field atrial cardiac signals are sensed using electrodes implanted within the ventricles and far-field ventricular cardiac signals are sensed using electrodes implanted within the atria. The far-field atrial signals and the far-field ventricular signals are then combined to emulate the surface EKG. In another example, near-field atrial cardiac signals are sensed using electrodes implanted within the atria and near-field ventricular cardiac signals are sensed using electrodes implanted within the ventricles. The near-field atrial signals and the near-field ventricular signals are then combined to emulate the surface EKG. In either case, by combining selected portions of signals sensed within the atria with selected portions of signals sensed within the ventricles, a reasonably accurate surface EKG emulation is thereby easily generated without the need for complex signal processing algorithms.

In accordance with a second general aspect, techniques are provided for emulating a surface EKG of a patient in which an implantable cardiac stimulation device is implanted using a single signal-based technique wherein portions of a single internal cardiac signal are selectively attenuated or amplified relative to other portions to yield the emulated EKG. Briefly, cardiac signals are sensed using one or more electrodes implanted within the heart. Portions of the cardiac signals corresponding to atrial signals are distinguished from those corresponding to ventricular signals. Then amplitudes of the portions of the cardiac signals corresponding to atrial signals and the portions corresponding to ventricular signals are adjusted relative to one another so as to yield the emulated surface EKG. Sensing may be performed, for example, by using an atrial unipolar lead by sensing "tip to case" or, as another example, by using separate atrial and ventricular unipolar leads and sensing "tip to tip" or "ring to ring". Herein, sensing of signals between a lead in the atria and a lead in the ventricles is referred to as "cross-chamber" sensing. By generating an emulated surface EKG by attenuating selected portions of a single internal cardiac signal relative to other portions, a reasonably accurate emulation may also be achieved again without requiring computationally-intensive techniques.

In one particular example, a cardiac signal is sensed using a unipolar atrial electrode and portions of the atrial unipolar signal corresponding to near-field atrial signals are distinguished from those corresponding to far-field ventricular signals. Then the amplitudes of the portions of the cardiac signal corresponding to near-field atrial signals and the portions corresponding to far-field ventricular signals are selectively adjusted relative to one another so as to yield the emulated surface EKG. In another example, a cross-chamber cardiac signal is sensed between an atrial electrode and a ventricular electrode. Portions of the cross-chamber signal corresponding to atrial signals are distinguished from those corresponding to ventricular signals and then amplitudes of the portions of the signal corresponding to atrial signals and the portions corresponding to ventricular signals are selectively adjusted relative to one another so as to yield the emulated surface EKG. Preferably, the atrial and ventricular portions are adjusted so as to achieve for a pre-determined ratio of peak atrial to peak ventricular signal amplitudes, typically in the rage of 1:4 to 1:10. In any case, by selectively adjusting the amplitudes of portions of cardiac signal arising from the atria relative to portions of cardiac signal arising from the ventricles, a reasonably accurate surface EKG emulation is thereby easily generated again without the need for complex signal processing algorithms.

Thus, in its various embodiments, the disclosed embodiments provide simple but effective techniques for emulating a surface EKG based on internally-detected cardiac signals. An important aspect is the recognition that emulation of a surface EKG can be easily generated either by concatenating selected portions of separate internal cardiac signals or by adjusting selected portions of a single internal cardiac signal, without requiring sophisticated signal processing techniques. The emulated surface EKG may be generated by an external programmer based on signals sent from an implanted device or may be generated by the implanted device itself for subsequent transmission to an external programmer for display. In either case, the need for a separate surface EKG system is eliminated. If generated by the implanted device itself, the emulated surface EKG may be used in conjunction with other cardiac signals for controlling operations of the device, such as delivery of therapy. Other objects, features and advantages will be apparent from the descriptions below in combination with the accompanying drawings.

BRIEF DESCRIPTION OF THE DRAWINGS

Further features and advantages of the illustrative embodiments may be more readily understood by reference to the following description taken in conjunction with the accompanying drawings, in which.

DESCRIPTION OF THE PREFERRED EMBODIMENTS

The following description includes the best mode presently contemplated of the described system and method. The description is not to be taken in a limiting sense but is made merely for the purpose of describing the general principles of the system and method. The scope of the invention should be ascertained with reference to the issued claims. In the description that follows, like numerals or reference designators will be used to refer to like parts or elements throughout.

Implantable Device Overview

Figure 1:
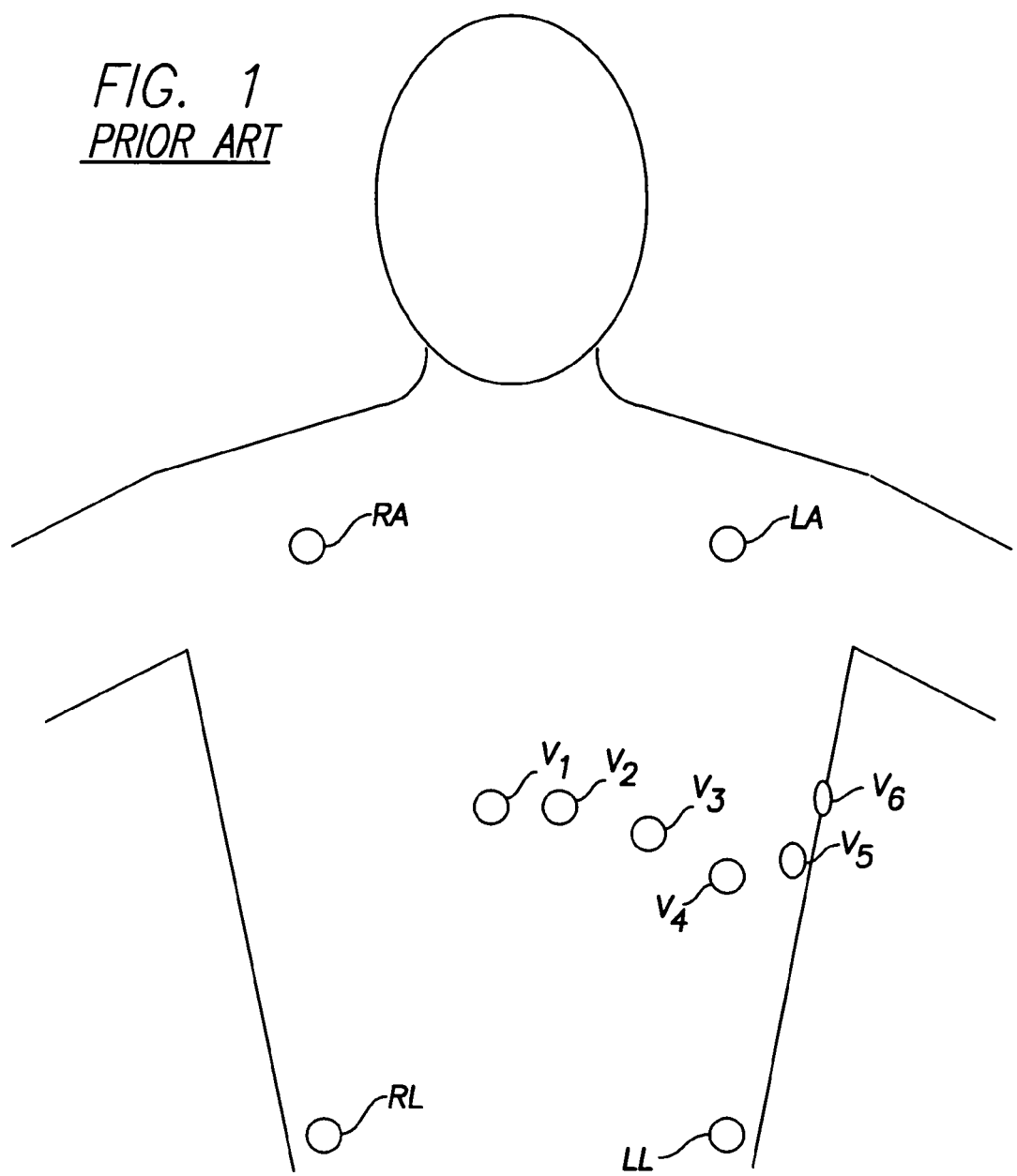
FIG. 1 is a diagram illustrating a system of electrodes for use in generating a surface EKG in accordance with the prior art.
Figure 2:
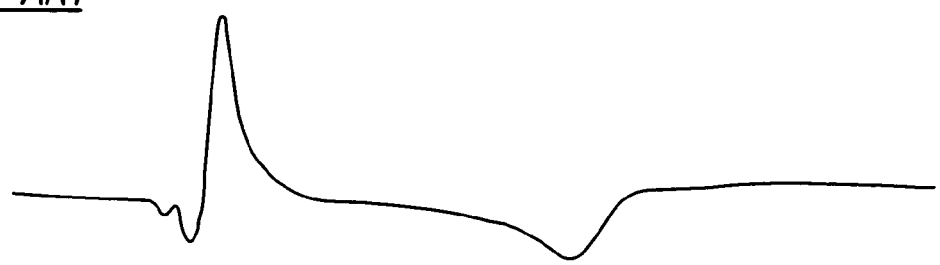
FIG. 2 is a graph illustrating an exemplary combined surface EKG derived from the electrodes of FIG. 1, also in accordance with the prior art.
Figure 3:
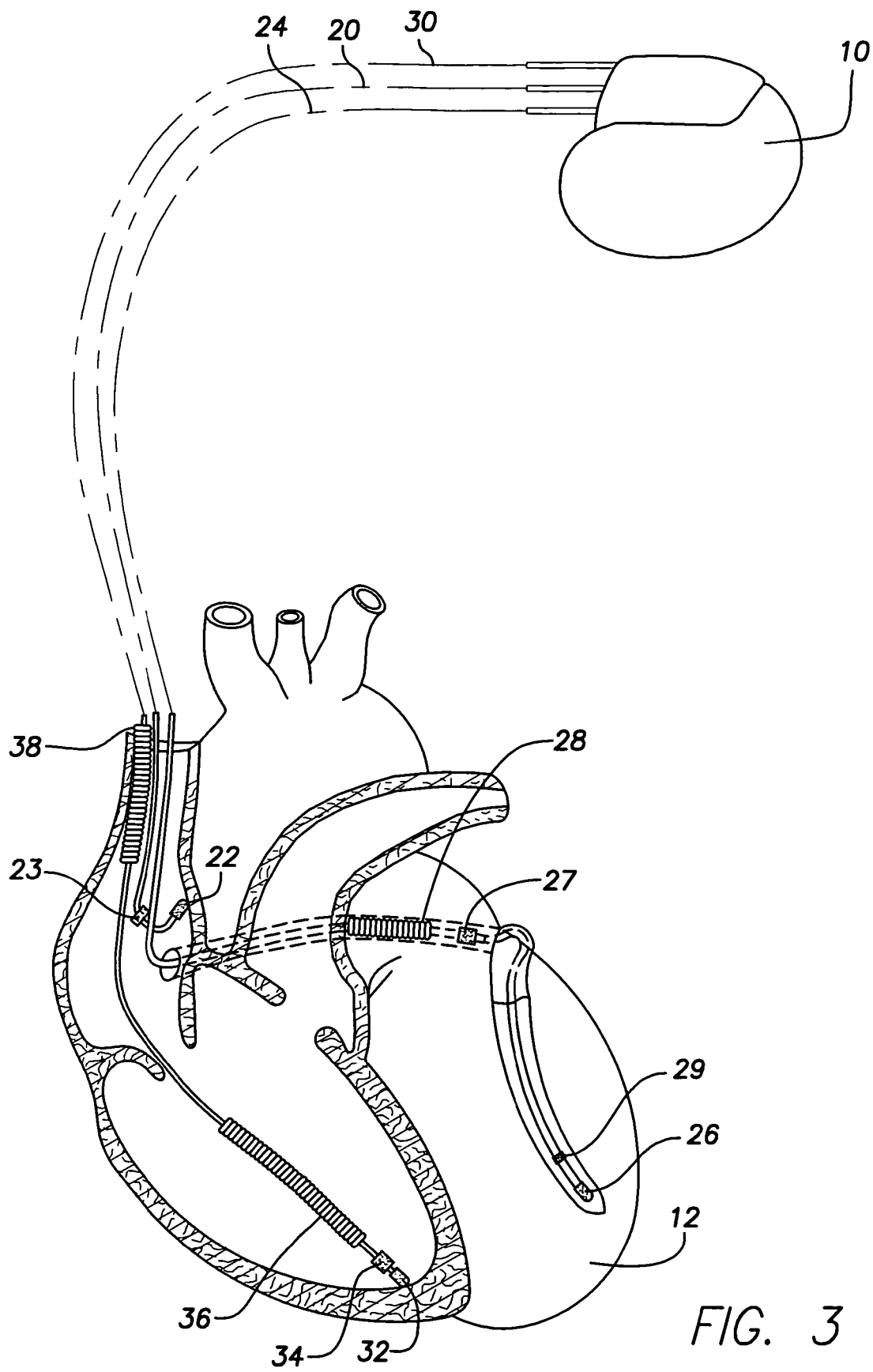
FIG. 3 is a simplified diagram illustrating an implantable stimulation device in electrical communication with at least three leads implanted into a patient's heart for delivering multi-chamber stimulation and shock therapy.

As shown in FIG. 3, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. A ring electrode 29 is also provided in the left ventricle on lead 24 to allow for bipolar left ventricular sensing. Additionally, although not specifically shown, epicardial electrodes, transseptal electrodes or other coronary sinus coil electrodes may be provided.

Figure 4:
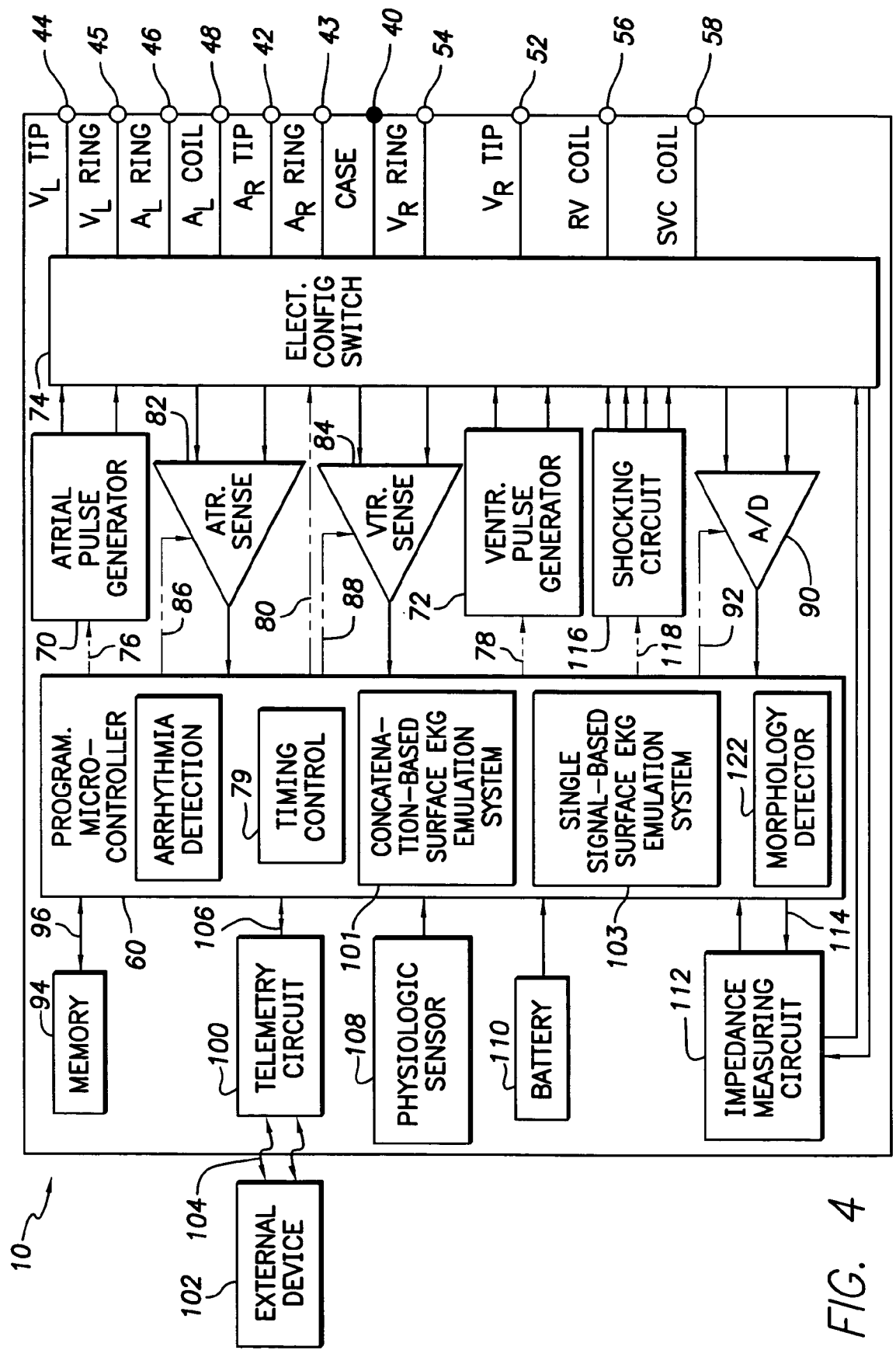
FIG. 4 is a functional block diagram of the multi-chamber implantable stimulation device of FIG. 3 illustrating the basic elements of a stimulation device which can provide cardioversion, defibrillation and pacing stimulation in four chambers of the heart and particularly illustrating an on-board surface EKG emulation system for emulating a single combined surface EKG based on far-field signals sensed using the implanted leads of FIG. 3.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle. Although not show, the system of leads may also include one or more RA rings in the proximal coronary sinus, one or more LV rings and an LV coil As illustrated in FIG. 4, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 4, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 45, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left ventricular ring terminal ($V_L$ RING) 45, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. Additional terminals may be provided for use with an LV coil or transseptal or epicardial electrodes.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the embodiments described herein. Rather, any suitable microcontroller 60 may be used that carries out the functions described herein. The use of microprocessor-based control circuits for performing timing and data analysis functions are well known in the art.

As shown in FIG. 4, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) evoked response windows, alert intervals, marker channel timing, etc., which is well known in the art. The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to sense voltages between any of the electrodes of the right atrial lead 20, coronary sinus lead 24, and the right ventricular lead 30, and the can, through the switch 74 for sensing the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), as is known in the art.

Microcontroller 60 includes a concatenation-based surface EKG emulation system 101, which operates to emulate a surface EKG based on signals received from the implanted electrodes, in accordance with a concatenation-based technique to be described in detail below with reference to FIGS. 6-15. Microcontroller 60 also includes a single signal-based surface EKG emulation system 103, which operates to emulate a surface EKG in accordance with a technique to be described in detail below with reference to FIGS. 16-22. Both systems are illustrated for the sake of completeness, though a typical implanted device will only be configured with one or the other. If both systems are provided, programming signals provided by the external programmer are employed to activate one or the other. Alternatively, the two systems can be combined into a single system. Also, although shown as components of the microcontroller, the emulation systems may be separate components.

For arrhythmia detection, the device 10 utilizes cardiac event detection unit 101 to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

In addition, the stimulation device may be configured to perform Automatic Mode Switching (AMS) wherein the pacemaker reverts from a tracking mode such as a VDD or DDD mode to a nontracking mode such as WI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both chambers but only paces in the ventricle. A sensed event on the atrial channel triggers a ventricular output after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

The stimulation device additionally includes a battery 110, which provides operating power to all of the circuits shown in FIG. 4. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 4, the device 10 is shown as having an impedance measuring circuit 112 which is enabled by the microcontroller 60 via a control signal 114. The impedance measuring circuit 112 is not critical to the embodiments described herein and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules) or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

External Programmer Overview

Figure 5:
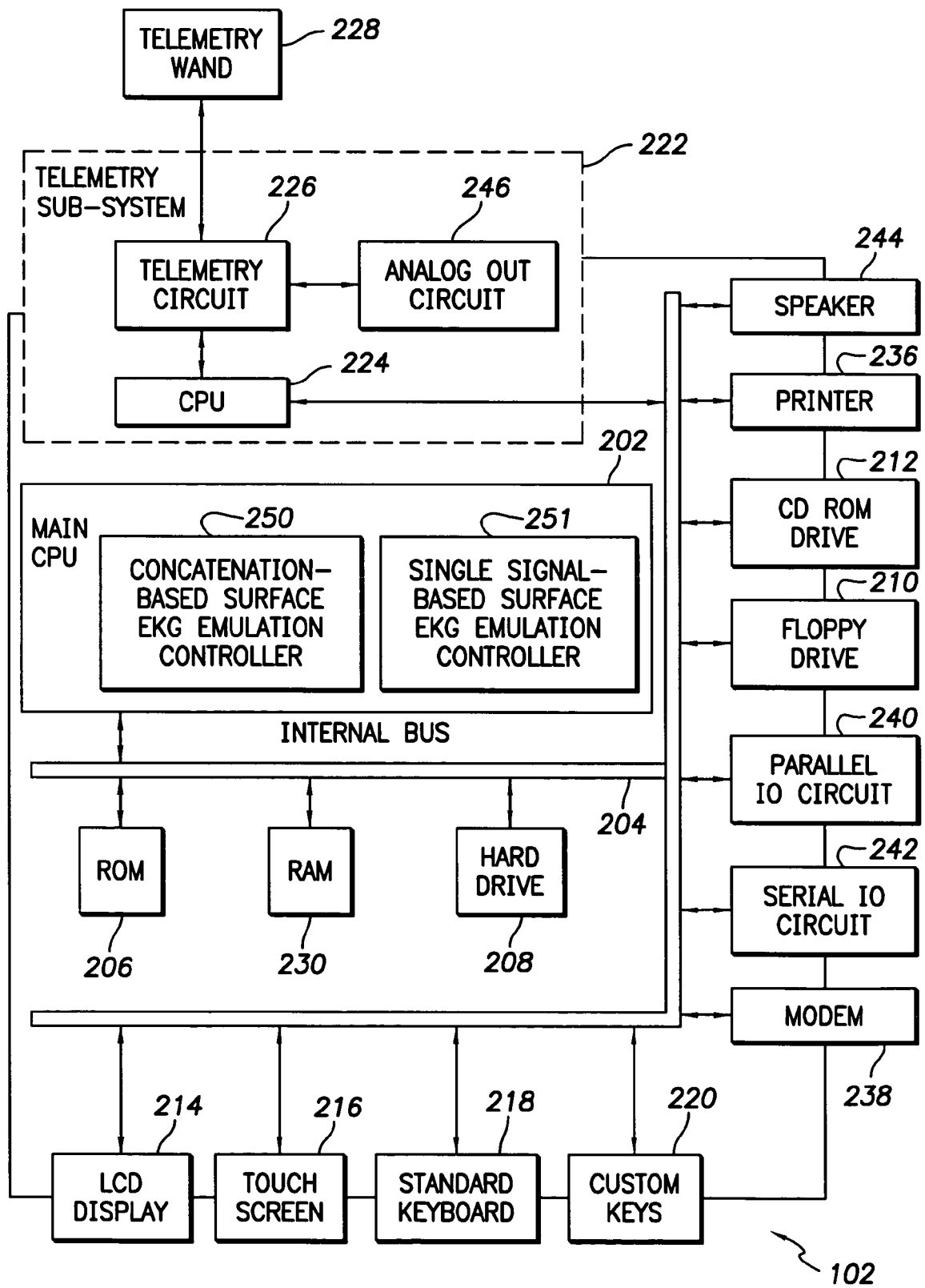
FIG. 5 is a functional block diagram illustrating components of a programmer for use in programming the implantable device of FIG. 3, and in particular illustrating a programmer-based surface EKG emulation system for emulating a single combined surface EKG based on far-field signals transmitted from the implanted device of FIG. 4 (and particularly for use with implantable devices that do not include an on-board surface EKG emulation system)

FIG. 5 illustrates pertinent components of an external programmer for use in programming an implantable medical device such as a pacemaker or ICD. Briefly, the programmer permits a physician or other user to program the operation of the implanted device and to retrieve and display information received from the implanted device such as IEGM data and device diagnostic data. Depending upon the specific programming of the external programmer, programmer 102 may also be capable of processing and analyzing data received from the implanted device to, for example, render preliminary diagnosis as to medical conditions of the patient or to the operations of the implanted device.

Now, considering the components of programmer 102, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206 and random access memory 230. Additional software may be accessed from a hard drive 208, floppy drive 210 and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Typically, the physician initially controls the programmer 102 to retrieve data stored within the implanted medical device. To this end, CPU 202 transmits appropriate signals to a telemetry subsystem 222, which provides components for directly interfacing with the implanted device. Telemetry subsystem 222 includes its own separate CPU 224 for coordinating the operations of the telemetry subsystem. Main CPU 202 of programmer communicates with telemetry subsystem CPU 224 via internal bus 204. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient near the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted device is stored by external programmer 102 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 102, the implanted device may be further controlled to transmit additional data in real time as it is detected by the implanted device, such as additional IEGM data, lead impedance data, and the like. Thus, the programmer receives data both from the implanted device. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Prior to reprogramming specific parameters, the physician may control the external programmer to display any or all of the data retrieved from the implanted device, including displays of IEGMs and statistical patient information. Any or all of the information displayed by programmer may also be printed using a printer 236.

CPU 202 includes a concatenation-based surface EKG emulation controller 250 for use in either controlling on-board concatenation-based system 101 to perform EKG emulation or for directly performing the EKG emulation itself based on signals detected by the implanted device using one of the concatenation techniques of FIGS. 6-15. The CPU also includes a single signal-based surface EKG emulation system 251 for use in either controlling on-board emulation system 103 to perform EKG emulation or for directly performing the EKG emulation itself based on signals detected by the implanted device using one of the single signal-based techniques of FIGS. 16-22. Systems 250 and 251 are both illustrated for the sake of completeness, though external programmers may be provided that include only one or the other. If both systems are provided, commands entered by the physician are employed to activate one or the other. Alternatively, the two systems can be combined into a single integrated system. Also, although shown as components of the microcontroller, the emulation systems may be separate components.

Figure 23:
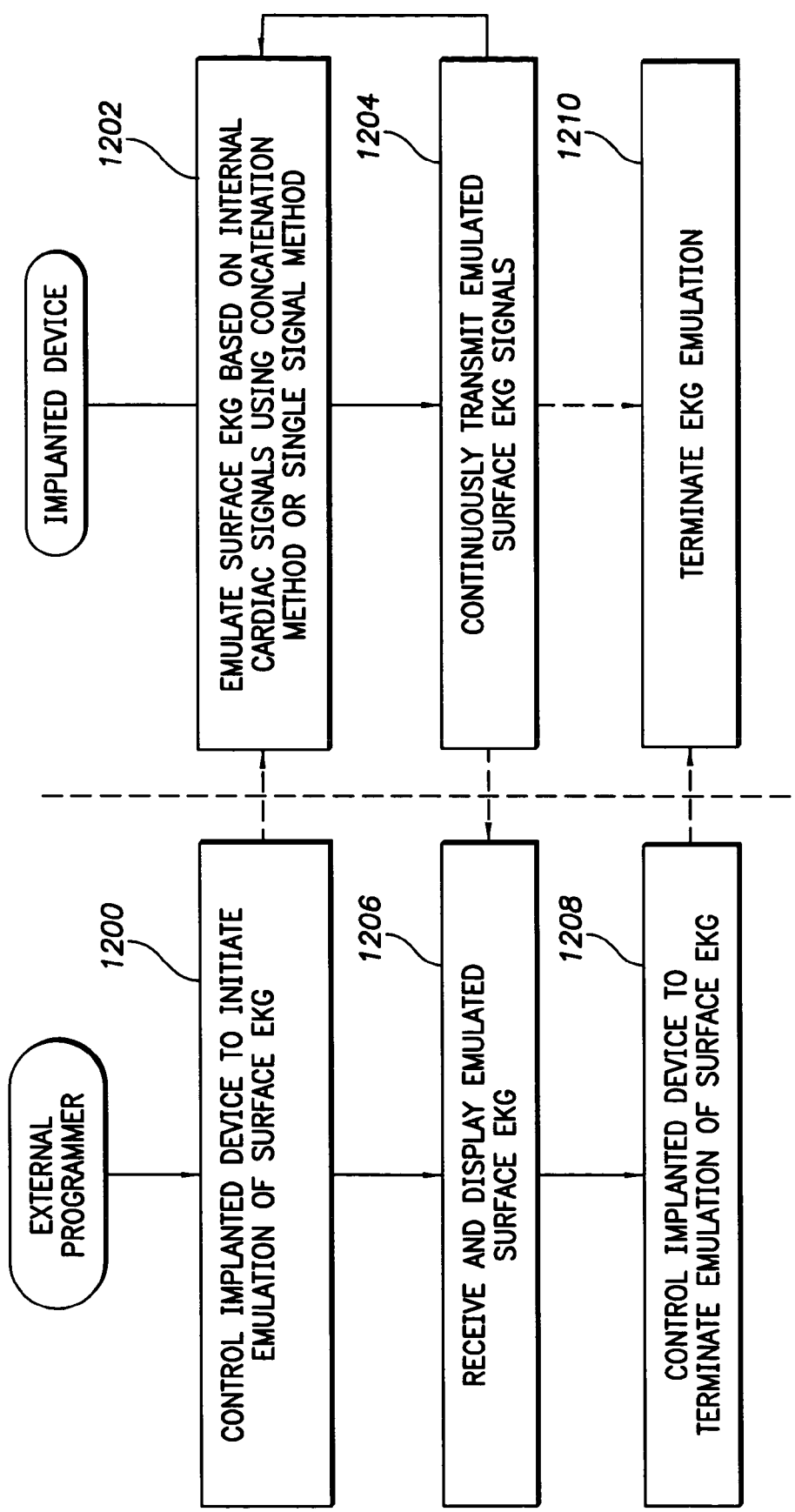
FIG. 23 is a flow chart illustrating a system implementation applicable to any of the emulation techniques described herein wherein the implanted device of FIG. 4 generates the emulated EKG for transmission to the external programmer of FIG. 5.
Figure 24:
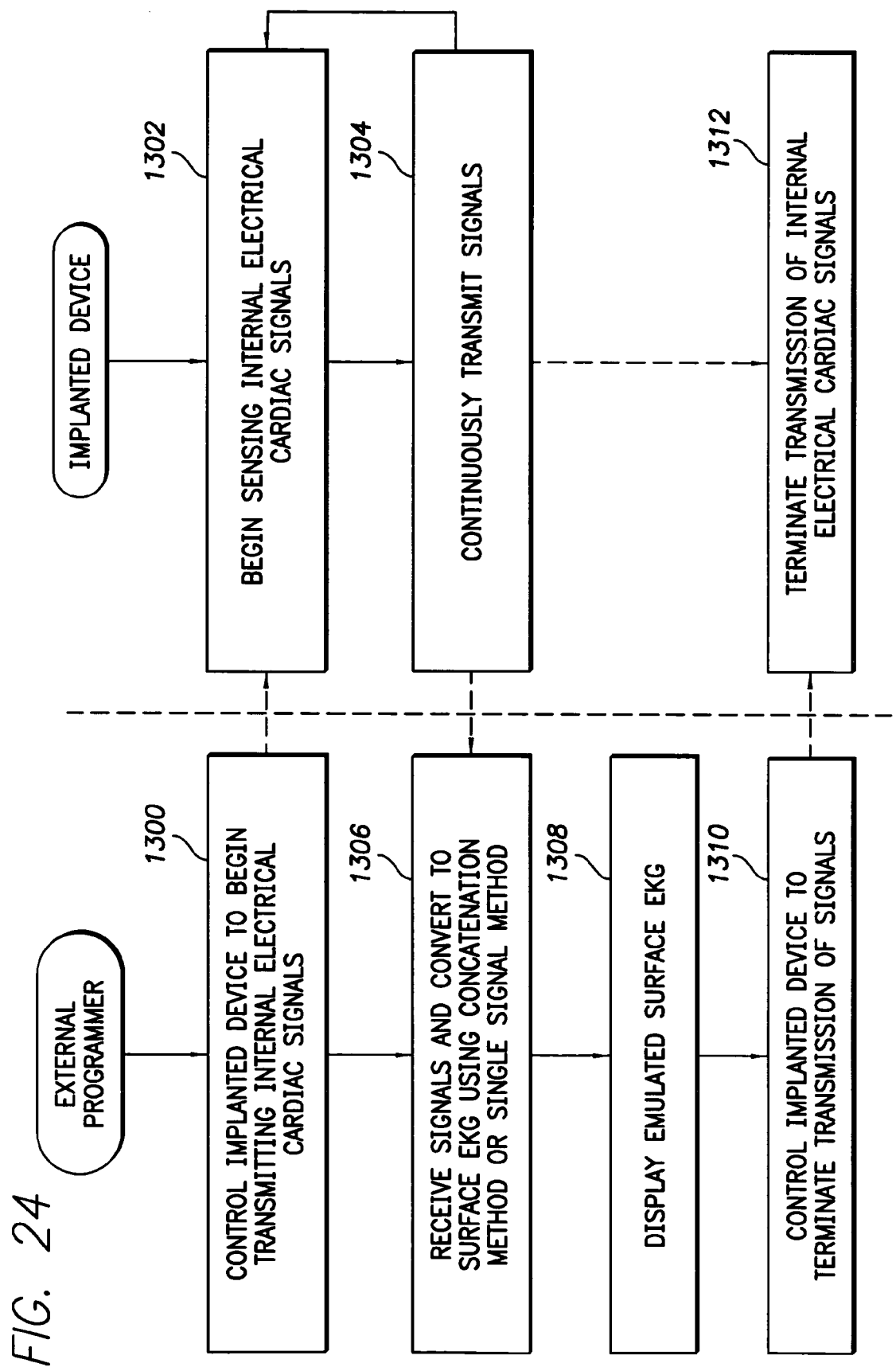
FIG. 24 is a flow chart illustrating a system implementation applicable to any of the emulation techniques described herein wherein the implanted device of FIG. 4 transmits internal cardiac signals to the external programmer of FIG. 5, which then generates the emulated surface EKG based on the signals.

FIG. 23 illustrates the operation of the external programmer and the implanted device for an embodiment wherein the implanted device performs the actual surface EKG emulation. FIG. 24 illustrates the operation of the external programmer and the implanted device for an embodiment wherein the external programmer performs the actual surface EKG emulation.

Programmer 102 also includes a modem 238 to permit direct transmission of data to other programmers via the public switched telephone network (PSTN) or other interconnection line, such as a T1 line or fiber optic cable. Depending upon the implementation, the modem may be connected directly to internal bus 204 or may be connected to the internal bus via either a parallel port 240 or a serial port 242. Other peripheral devices may be connected to the external programmer via parallel port 240 or a serial port 242 as well. Although one of each is shown, a plurality of input output (IO) ports might be provided. A speaker 244 is included for providing audible tones to the user, such as a warning beep in the event improper input is provided by the physician. Telemetry subsystem 222 additionally includes an analog output circuit 246 for controlling the transmission of analog output signals, such as emulated EKG signals output to an EKG machine or chart recorder.

With the programmer configured as shown, a physician or other user operating the external programmer is capable of retrieving, processing and displaying a wide range of information received from the implanted device and to reprogram the implanted device if needed. The descriptions provided herein with respect to FIG. 5 are intended merely to provide an overview of the operation of programmer and are not intended to describe in detail every feature of the hardware and software of the device and are not intended to provide an exhaustive list of the functions performed by the device.

The operations of the implanted device of FIG. 4 and the external programmer of FIG. 5 for emulating surface EKG signals will now be described with references to the remaining figures, which include various flow-charts. In the flow charts, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device or external programmer. Those skilled in the art may readily write such a control program based on the flow charts and other descriptions presented herein.

Figure 6:
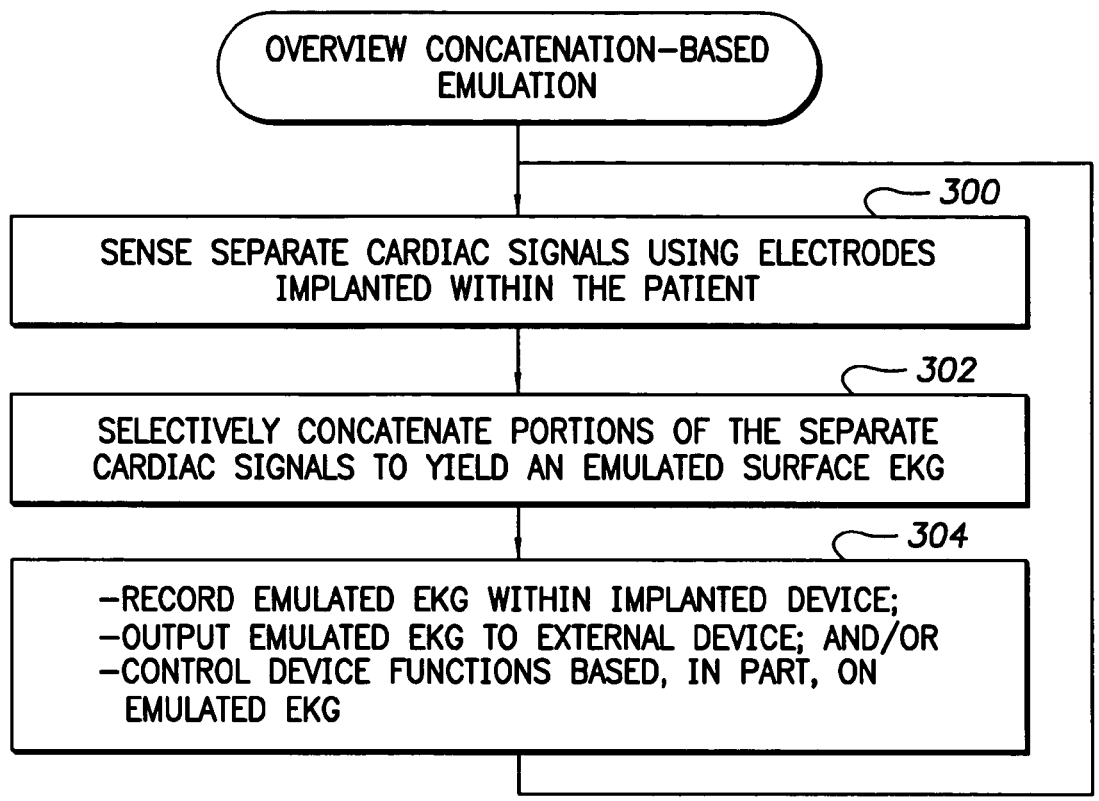
FIG. 6 is a flow chart providing an overview of an exemplary concatenation-based technique for emulating a surface EKG for use either by the on-board surface EKG emulation system of FIG. 4 or the programmer-based surface EKG emulation system of FIG. 5.

Overview of Multiple Signal-Based Concatenation Techniques for Emulating a Surface EKG FIG. 6 provides an overview of the concatenation-based technique wherein portions of at least two separate internal cardiac signals are concatenated together to yield an emulated surface EKG. As noted above, the general technique can be performed either by the on-board concatenation-based emulation system of the implanted device (system 101 of FIG. 4) or by the concatenation-based emulation controller of the external programmer (system 250 of FIG. 5). In the following, it will be assumed that the emulation is performed by the on-board system of the implanted device but the description is generally applicable to the programmer-based system of the external programmer. Briefly, at step 300, separate cardiac signals are sensed using electrodes implanted within the patient (such as an atrial channel signal sensed between atrial tip electrode 22 and the device housing and a separate ventricular channel signal sensed between ventricular tip electrode 32 and the device housing.) Then, at step 302, portions of the separate cardiac signals sensed are selectively concatenated to yield an emulated surface EKG. After the surface EKG has been emulated then, at step 304, the implanted device records the emulated EKG within its internal memory and/or outputs the emulated EKG to an external programmer for display thereon. In addition, depending upon the implementation, certain functions of the implanted device itself may be controlled, in part, based on the features of the emulated surface EKG. In this regard, device functions are preferably controlled by the microcontroller based primarily on IEGM signals. However, circumstances may arise wherein the analysis of IEGM signals fails to allow the microcontroller to unambiguously determine the appropriate therapy to deliver to the patient (such as to determine, for example, whether the patient is undergoing atrial fibrillation for purposes of triggering delivery of a cardioversion shock) and further analysis of the emulated surface EKG can help the system select the correct course of therapy.

Herein, two specific examples of concatenation-based emulation are described. The first, based on concatenating far-field signals, is described with reference to FIGS. 7-12. The second, based on concatenating near-field signals, is described with reference to FIGS. 13-15.

Emulation Based on Concatenated Far-Field Signals

Figure 7:
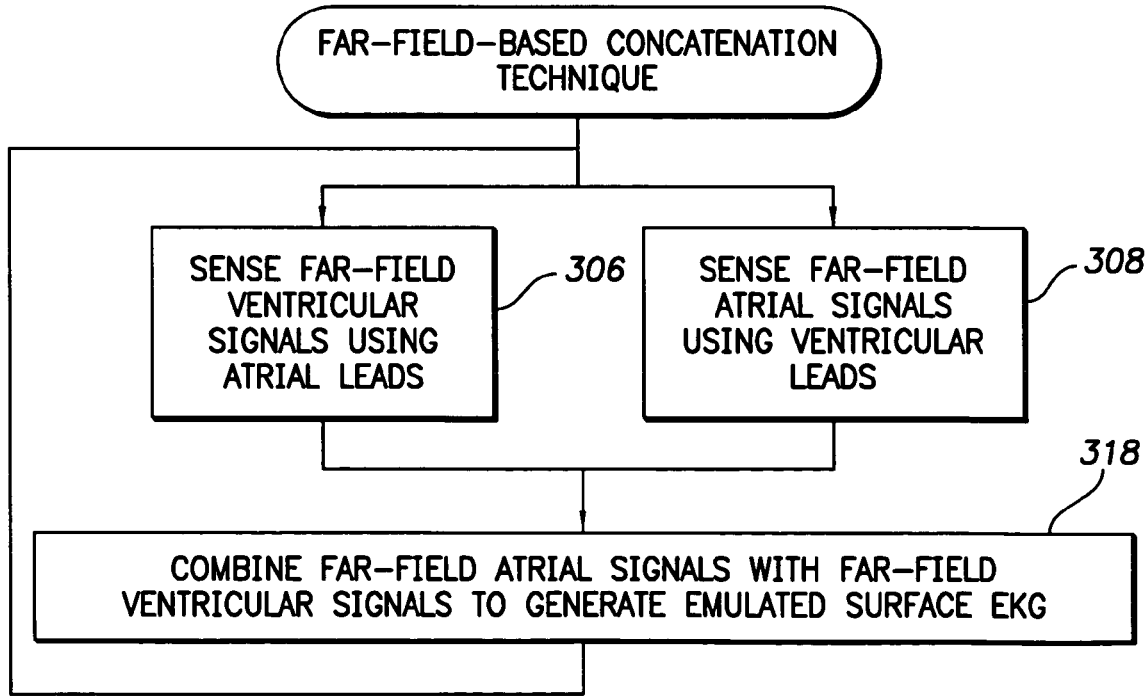
FIG. 7 is a flow chart summarizing a far-field-based concatenation technique, which is an example of the general concatenation technique of FIG. 6.
Figure 8:
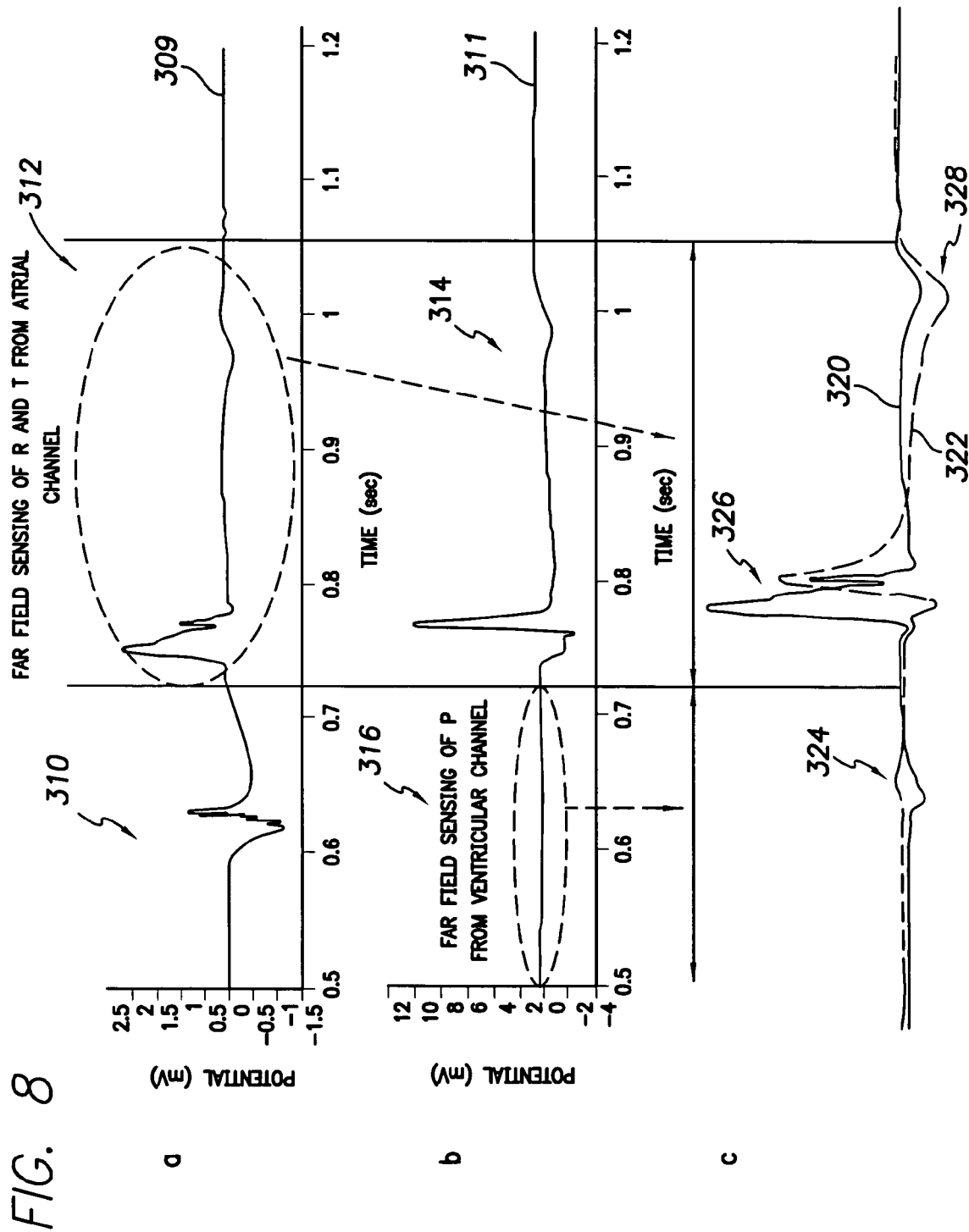
FIG. 8 is a diagram illustrating separate ventricular and atrial channel signals and an emulated surface EKG derived from the separate signals using the far-field technique of FIG. 7.

The far-field-based technique is summarized in FIGS. 7-8. Briefly, the technique operates to emulate a surface EKG by combining far-field ventricular signals sensed in the atria with far-field atrial signals sensed in the ventricles. Simultaneously, at steps 306 and 308 of FIG. 7, the implanted device senses far-field ventricular signals using atrial leads and senses far-field atrial signals using ventricular leads. This may be achieved by sensing both near-field and far-field signals then extracting only the far-field signals. FIG. 8 illustrates an atrial channel IEGM signal 309 sensed using a unipolar lead implanted in the atria and also illustrates a ventricular channel IEGM signal 311 sensed using a unipolar lead implanted within the ventricles. As can be seen, the atrial and ventricular IEGM signals both include near-field and far-field signal portions. More specifically, atrial IEGM signal 309 includes a first portion 310 corresponding to near-field signals generated in the atria and a second portion 312 corresponding to far-field signals generated in the ventricles. The near-field signals sensed in the atrial are representative of local electrical activity in tissue near the atrial electrode; whereas the far-field signals are representative of the global electrical activity of the ventricles. Conversely, ventricular IEGM signal 311 includes a first portion 314 corresponding to near-field signals generated in the ventricles and a second portion 316 corresponding to far-field signals generated in the atria. The near-field signals sensed in the ventricles are representative of local electrical activity in tissue near the ventricular electrode; whereas the far-field signals are representative of the global electrical activity of the atria. Note that, although embodiments are described herein wherein a pair of separate atrial and ventricular channels is employed, this is merely exemplary. The implanted device may have more or fewer channels, which may be reassigned as needed.

At step 318 of FIG. 7, the implanted device combines far-field ventricular signals 312 with far-field atrial signals 316 to yield an emulated surface EKG 320 (shown in FIG. 8.) An actual surface EKG 322 is also provided in dashed lines for comparison. As can be seen, the emulated surface EKG provides a reasonably accurate approximation of the surface EKG, which is at least sufficient to allow easy identification of major features, such as P-wave 324, QRS complex 326 and T-wave 328. (Note that the R-wave portion of emulated EKG 320 is slightly offset from the corresponding R-wave portion of atrial channel signal 309 and the P-wave portion of emulated EKG 320 is slightly offset from the corresponding P-wave portion of ventricular channel signal 311 due to slight timing differences caused by sensing signals using different electrodes.) In the example, of FIG. 8, the polarity of the P-wave is reversed between the emulated surface EKG and the actual surface EKG. If desired, at step 318 of FIG. 7, the polarity of either far-field ventricular signals 312 or far-field atrial signals 316 can be reversed to ensure that the P-wave and R-wave peaks of the emulated surface EKG have the same polarity. In addition, preferably, the relative amplitudes of the atrial and ventricular portions are adjusted to achieve a predetermined ratio of peak amplitudes, such as a ratio of 1:4 or 1:10 of average P-wave peak to average R-wave peak. To this end, the peaks amplitudes of the P-wave and R-waves are calculated and a running average is maintained so that the relative amplitudes may be automatically adjusted to maintain the desired ratio. As shown in FIG. 6, after the surface EKG has been emulated then, the implanted device can record the emulated EKG within its internal memory, output the emulated EKG to an external programmer for display thereon and/or control certain functions of the implanted device including delivery of therapy.

By selectively combining far-field atrial signals sensed using ventricular leads with far-field ventricular signals sensed using atrial leads, a reasonably accurate emulation of a surface EKG is thereby quickly and easily generated. No sophisticated signal processing techniques are needed and no significant memory or computational resources are required. Hence, the technique allows surface EKG emulation to be provided within implanted devices that do not have sufficient memory or computational resources to permit the incorporation of more complex surface EKG emulation algorithms. Note that, in some implementations, when the technique is performed by the implanted device it does so only while in communication with the external programmer. In other words, the on-board emulation system only emulates the surface EKG signals while in telemetry contact with the external programmer. Hence, in those implementations, the implanted device need only transmit the emulated surface EKG signals to the external programmer and need not store the emulated EKG within memory. However, in other implementations, the on-board emulation system operates to emulate the surface EKG at all times. The emulated surface EKG is stored within the memory of the implanted device for subsequent transmission to the external programmer, perhaps during a follow-up session with the physician. In this manner, a diagnostic record of the emulated surface EKG of the patient is recorded within the implanted device (limited only by the memory constraints of the implanted device) for subsequent review by the physician.

Figure 9:
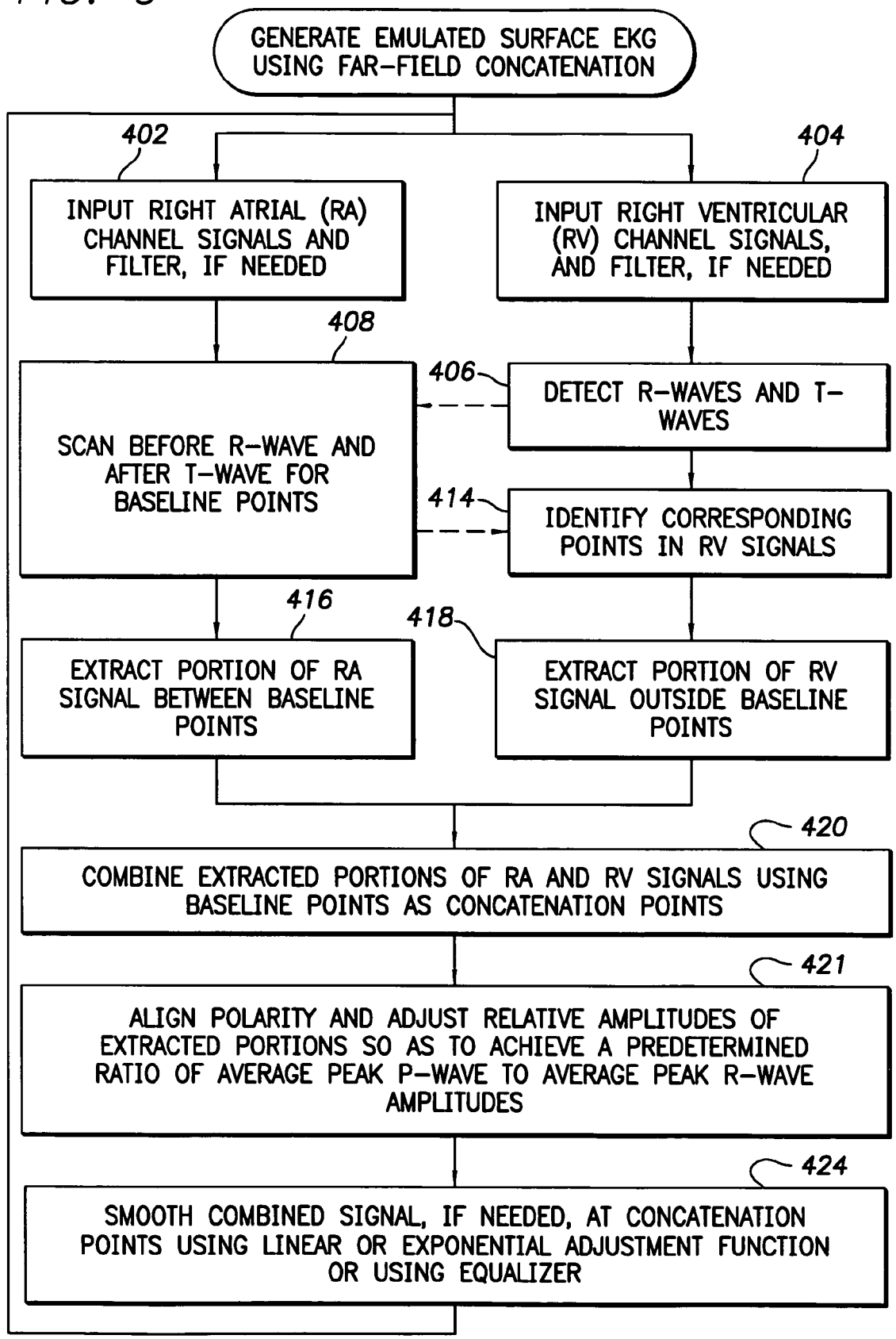
FIG. 9 is a flow chart providing details of the exemplary far field-based technique of FIG. 7.
Figure 10:
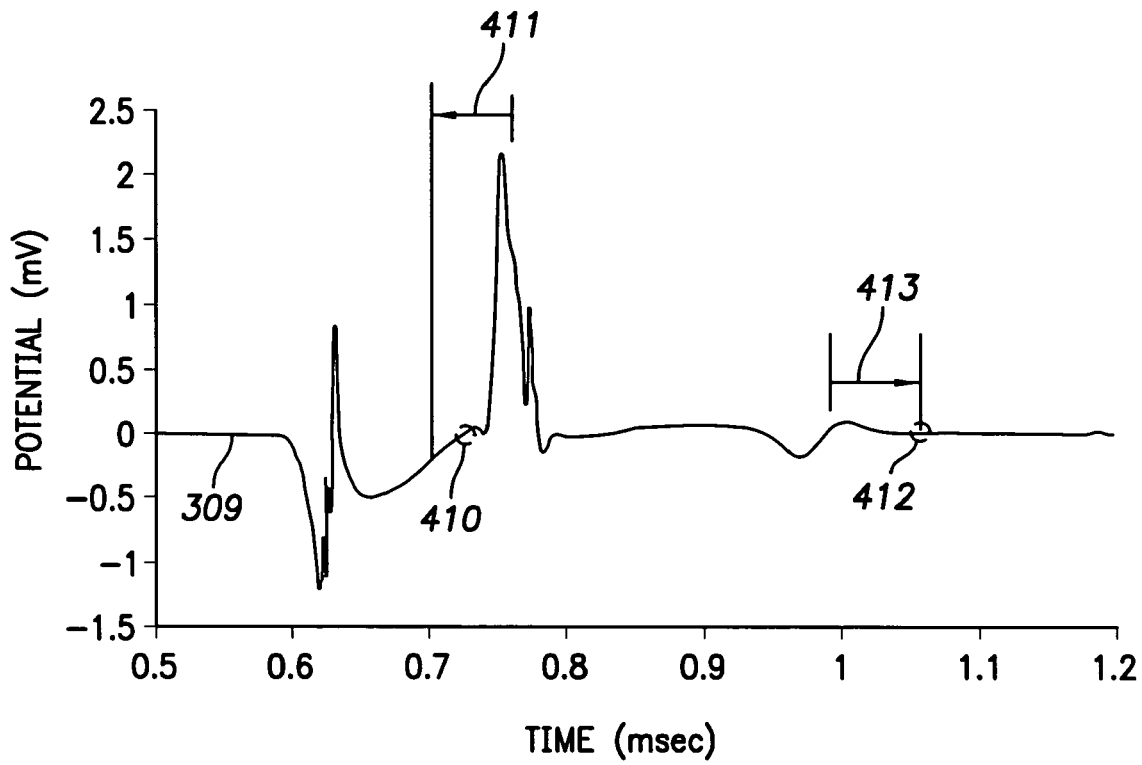
FIG. 10 is a diagram illustrating exemplary concatenation points identified using the technique of FIG. 9.

Referring to FIGS. 9-12, the far-field concatenation-based emulation technique will now be described in greater detail and, in particular, specific techniques for identifying concatenation points and for smoothing the resulting concatenated signal will be described. Referring first to FIG. 9, simultaneously, at steps 402 and 404, the emulation system inputs right atrial (RA) signals and right ventricular (RV) signals. The right ventricular signals may be sensed in using any of electrodes 32, 34 or 36 (FIG. 3) in unipolar sensing mode. That is, voltage differences between the electrode and the device can are sensed. Right atrial signals are sensed using leads 22 or 23 in unipolar sensing mode. At step 402 and 404, the RA and RV signals may be filtered using a high pass filter. Then, at step 406, the right ventricular channel signals are processed to detect the peaks of near-field R-waves and T-waves therein, using otherwise conventional event detection techniques. Alternatively, the system can be configured to detect the R-wave and T-wave within the atrial channel signals in unipolar mode. In order to identify concatenation points for concatenating far-field portions of the atrial and ventricular channel signals, step 408 is then performed wherein the RA channel signals preceding the R-wave peak and following the T-wave peak are scanned to identify baseline points. That is, the RA channel signal is scanned within a pre-R-wave window and is also scanned within a post-T-wave window to identify points at which the RA channel signal crosses a baseline voltage, such as 0.0 V. Other techniques for identifying baseline points may be employed as well. For example, a baseline point may be specified based on some amount of time following detection of an event, such as 300 milliseconds (ms) following detection of an R-wave. In one specific example, to determine the second baseline point, the device looks at the duration of the previous R-R interval and then calculates a delay value based on the R-R interval. The delay value specifies the time delay from the R-wave to the second baseline point. The delay value is calculated by multiplying the R-R interval by a programmable factor (such as 0.4) to yield, in one example, a delay value of 400 ms.

FIG. 10 again illustrates exemplary RA channel signal 309 (also shown in FIG. 8) and specifically shows a first baseline point 410, found within a pre-R-wave window 411, and a second baseline point 412, found within a post-T-wave window 413. Once the baseline points have been identified within the RA channel signals for a given heart beat, corresponding points in time within the RV channel signals are identified, at step 414. Then portions of the RA channel signals occurring between the pair of baseline points are extracted, at step 416. Simultaneously, portions of the RV channel signals occurring outside of the baseline points are extracted, at step 418. At step 420, the extracted portions of the RA and RV signals for the given heart beat are combined using the baseline points as concatenation points. At step 421, the relative polarities and the relative amplitudes of the signals may be adjusted. As noted, the polarities may be adjusted to ensure that both P-waves and the R-waves and the same polarity and the relative amplitudes may be adjusted so as to achieve a programmed ratio of average peak P-wave to average peak R-wave amplitudes.

Figure 11:
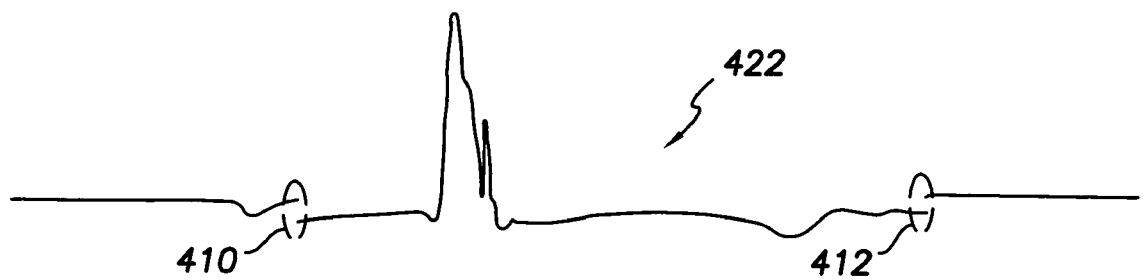
FIG. 11 is a diagram illustrating far-field atrial and ventricular signals concatenated using the technique of FIG. 9 and in particular showing slight discontinuities at concatenation points.
Figure 12:
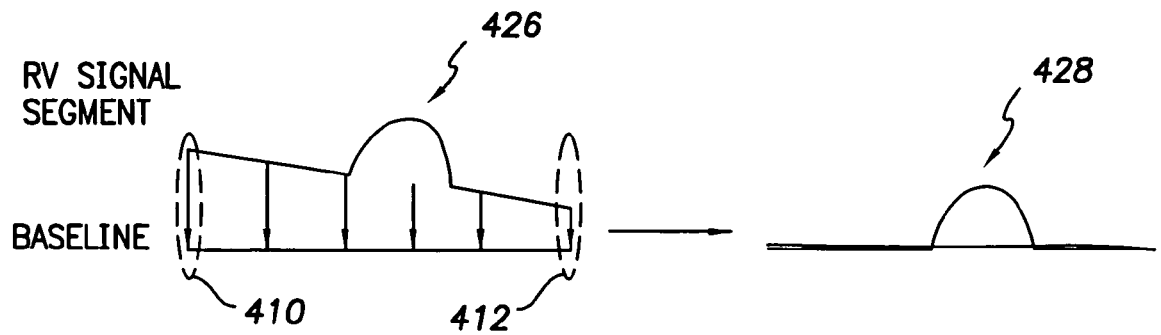
FIG. 12 is a diagram illustrating the smoothing of concatenated signals in accordance with the technique of FIG. 9.

An exemplary resulting concatenated signal, 422, for a single heart beat is shown in FIG. 11. As can be seen, slight discontinuities appear at concatenation points 410 and 412, which arise from signal voltage differences between the RA and RV cannel signals at those points. The concatenated signal is smoothed, at step 424 of FIG. 9, to eliminate any such discontinuities. To this end, portions of the combined signal derived from the RV channel are increased or decreased as needed to provide for smooth concatenation. For the specific example of FIG. 11, wherein the signals derived from the RV channel are all offset by equal amounts, the signals can merely be shifted upwardly or downwardly by equal amounts. That is, for a given heart beat, the amplitude of the signal on the RV channel at the concatenation point is determined and then this amount is subtracted from the far-field RV channel signals that used to form the emulated surface EKG. The resulting, smoothed concatenated signal is shown in FIG. 8 as solid line 320. In other cases, the RV channel signals may not all be shifted by equal amounts. Rather, the amount of offset at one concatenation point may be greater than the offset at an adjacent concatenation point. This is illustrated in FIG. 12 by exemplary RV far-field signal segment 426, which includes a far-field P-wave. As can be seen, opposing ends of the segment vary from the baseline voltage by differing amounts. In this case, a linear function is determined based on the RV signal amplitudes at the adjacent concatenation points and the linear function is then used to adjust the amplitudes of individual points along the segment to eliminate discontinuities at both ends points. The adjusted RV signal segment is shown in FIG. 12 as segment 428.

In other embodiments, more sophisticated smoothing techniques may be employed to eliminate discontinuities. For example, an exponential decay function with the same time constant as that of a high pass filter through which the IEGM signals are processed (at steps 402 and 404) may be employed to remove any distortion associated with the filter. A starting amplitude of the exponential decay is set equal to the difference between the starting and ending amplitudes of the RV channel signal segment such that the transformation assures that the adjusted segment begins and ends at baseline voltage values. Note however, that techniques that exploit voltage differences at both ends of the RV channel segment cannot be performed in real-time because of the smoothing cannot be accomplished until the end points of the segment have been identified. Hence, a slight delay occurs between the heart beat of the patient and the emulated surface EKG. In still another embodiment, the starting amplitude of the exponential decay is set equal to the amplitude at the start of the RV channel signal segment relative to baseline and the adjustment is applied in real-time. However, with this technique, there is no assurance that the end of the adjusted RV signal segment will necessarily be reset exactly to the baseline value. In many cases, the adjustment is sufficient to remove most of the discontinuity at the end point and hence is suitable for surface EKG emulation purposes.

In an alternative technique, rather than examine discontinuities in the concatenation points and then adjust the RV channel signal segment, an equalizer is employed. The equalizer has a transfer function that is substantially the reciprocal of the high pass characteristic of the filter employed at steps 402 and 404. Its function is to restore low-frequency content removed by the filter so as to bring the pre-R wave and post-T wave concatenation points of both atrial and ventricular signals closer together.

An exemplary transfer function is:

$$H(jw) = \{((1+jw/w_1)/(jw/w_1))((jw/w_2)/(1+jw/w_2))\}^2$$

where $w_1 = 2\pi*1$ Hz is an upper frequency breakpoint corresponding to the high pass filter cutoff frequency of the channel and $w_2 = 2\pi*0.2$ Hz is a lower frequency breakpoint to provide limited gain at direct current (DC), and below which there is not expected to be significant information in an 8-bit system (such as those currently employed). The equalizer boosts the gain from 1 Hz to 0.2 Hz with a 40 dB/decade slope. The gain at 0.2 dB applies to all frequencies below and up to DC. These parameters are appropriate for use with currently available pacemakers and ICDs and are merely exemplary. Routine experimentation may be provided for other devices to identify parameters suitable for restoring as much low frequency content as possible with minimal distortion within those devices.

Another exemplary equalizer transfer function is:

$$H(jw) = \{((1+jw/w_1)/(jw/w_1))((jw/w_2)/(1+jw/w_2))\}^2 \\ ((jw/w_2)/(1+jw/w_2))$$

where the additional factor provides for attenuated gain below 0.2 Hz, thus eliminating the gain at DC that could otherwise cause a large DC offset of the output with only a small DC offset at the input, which may be unavoidable.

This latter equalizer technique has the advantage in that it enables the surface EKGs to be emulated substantially in real-time. Other smoothing techniques maybe employed as well, as will be apparent to those skilled in the art.

Emulation Based on Concatenated Near-Field Signals

Figure 13:
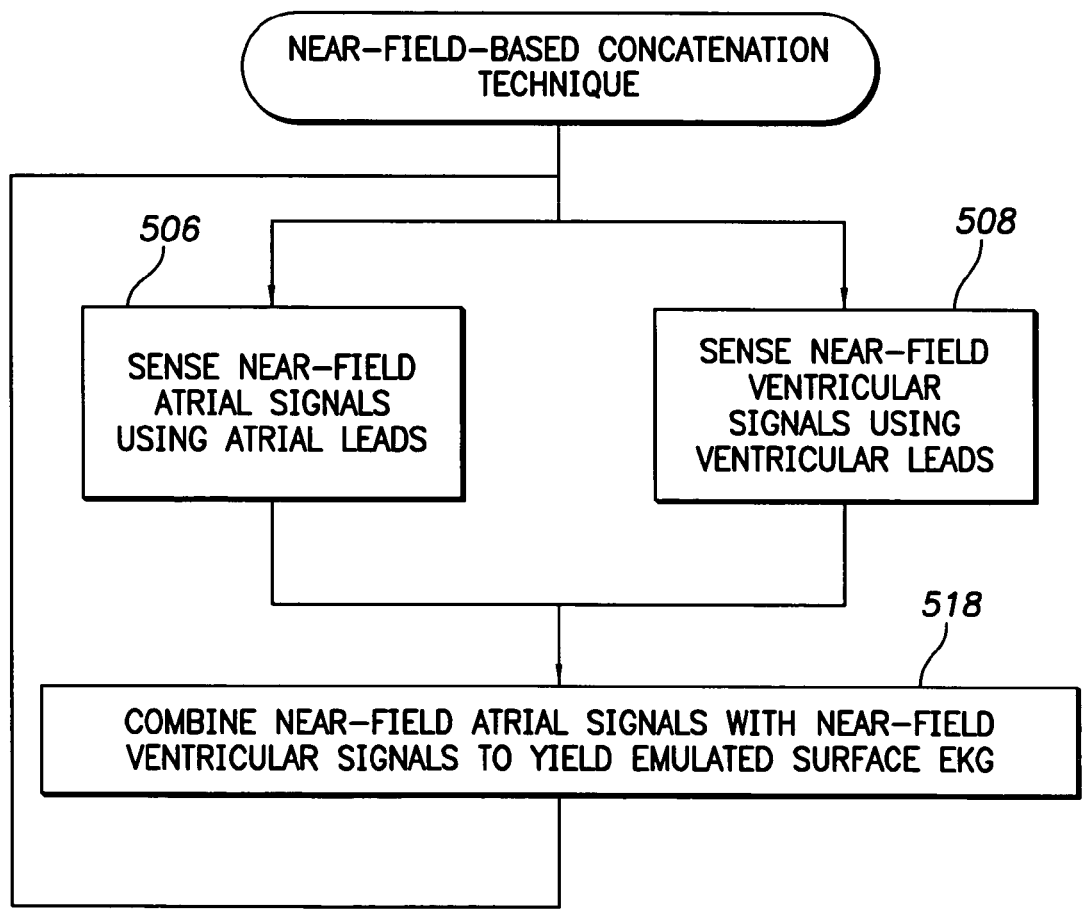
FIG. 13 is a flow chart summarizing a near-field-based concatenation technique, which is another example of the general concatenation technique of FIG. 6.
Figure 14:
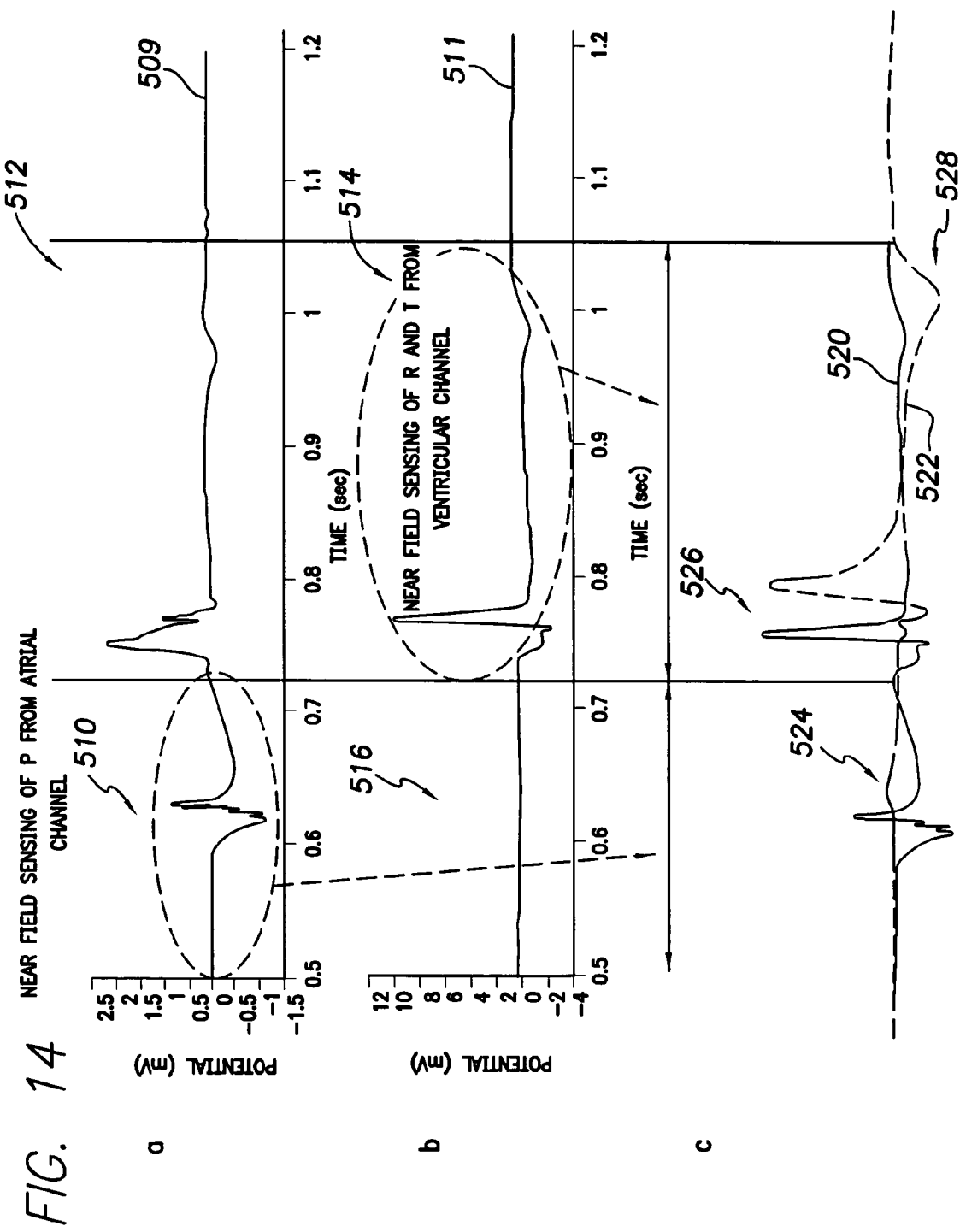
FIG. 14 is a diagram illustrating separate ventricular and atrial channel signals and an emulated surface EKG derived from the separate signals using the near-field concatenation technique of FIG. 13.

The near-field-based technique is summarized in FIGS. 13-14. Briefly, the technique operates to emulate a surface EKG by combining near-field atrial signals sensed in the atria with near-field ventricular signals sensed in the ventricles. Simultaneously, at steps 506 and 508 of FIG. 13, the implanted device senses near-field atrial signals using atrial leads and senses near-field ventricular signals using ventricular leads. This may be achieved by sensing both far-field and near-field signals then extracting only the near-field signals. FIG. 14 illustrates an atrial channel IEGM signal 509 sensed using a unipolar lead implanted in the atria and also illustrates a ventricular channel IEGM signal 511 sensed using a unipolar lead implanted within the ventricles. As before, the atrial and ventricular IEGM signals both include far-field and near-field signal portions. Atrial IEGM signal 509 includes a first portion 510 corresponding to near-field signals generated in the atria and a second portion 512 corresponding to far-field signals generated in the ventricles. Conversely, ventricular IEGM signal 511 includes a first portion 514 corresponding to near-field signals generated in the ventricles and a second portion 516 corresponding to far-field signals generated in the atria.

At step 518 of FIG. 13, the implanted device combines near-field atrial signals 510 with near-field ventricular signals 514 to yield an emulated surface EKG 520 (shown in FIG. 14.) An actual surface EKG 522 is also provided in dashed lines for comparison. As with the far-field technique described above, the emulated surface EKG generated by the near-field technique provides a reasonably accurate approximation of the surface EKG, which is again sufficient to allow easy identification of major features, such as P-wave 524, QRS complex 526 and T-wave 528. Again, if warranted, the polarity of either near-field atrial signals 510 or near-field ventricular signals 514 can be reversed to ensure that the P-wave and R-wave peaks of the emulated surface EKG have the same polarity. In addition, the relative amplitudes of the atrial and ventricular portions may be adjusted to achieve a predetermined ratio of peak amplitudes, such as a ratio of 1:4 or 1:10 of average P-wave peak to average R-wave peak. By selectively combining near-field atrial signals sensed using atrial leads with near-field ventricular signals sensed using ventricular leads, a reasonably accurate emulation of a surface EKG is thereby quickly and easily generated without requiring sophisticated signal processing techniques and without placing significant demands on memory or computational resources. In any case, as shown in FIG. 6, after the surface EKG has been emulated then, the implanted device can record the emulated EKG within its internal memory, output the emulated EKG to an external programmer for display thereon and/or control certain functions of the implanted device including delivery of therapy.

Figure 15:
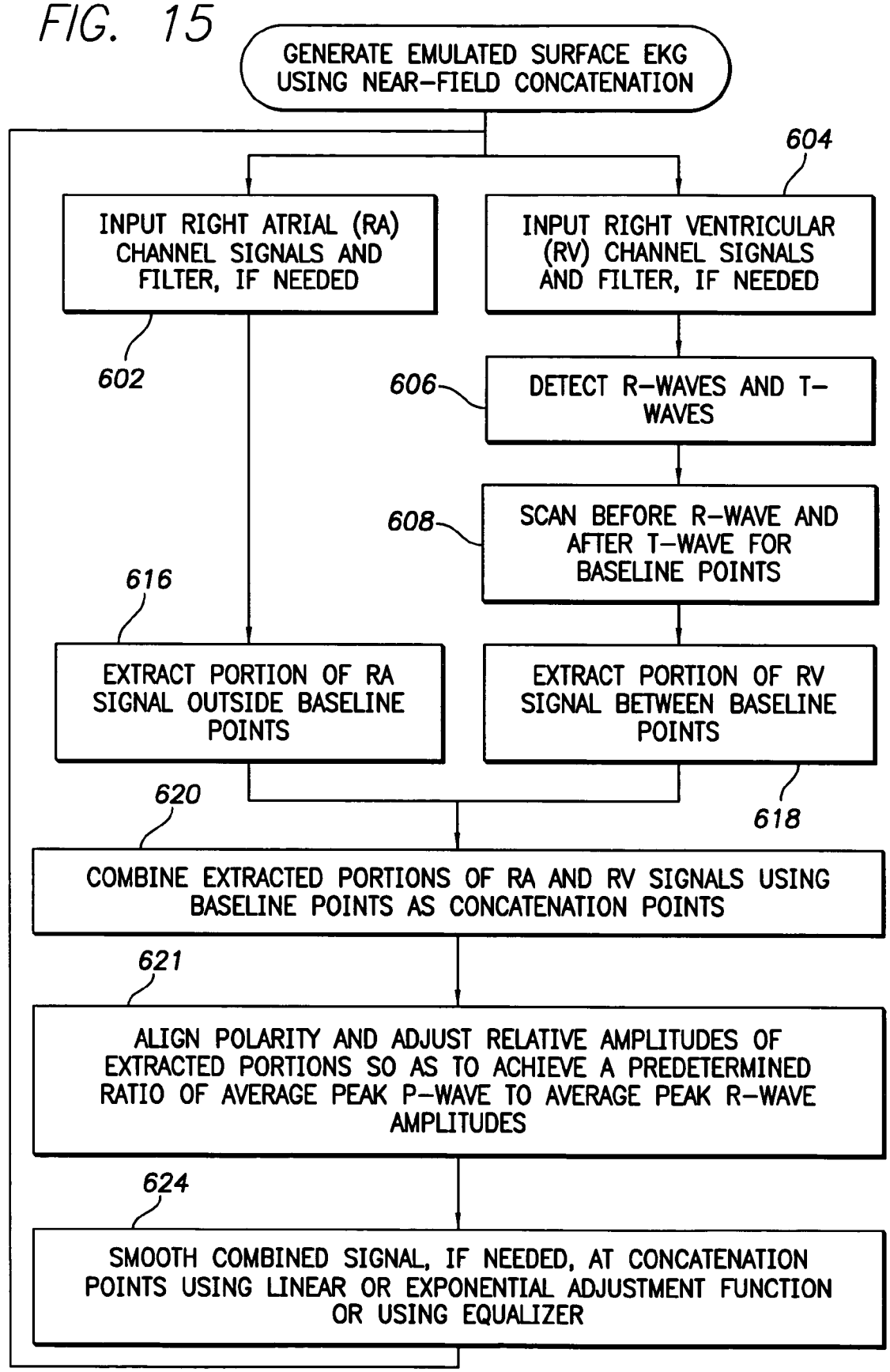
FIG. 15 is a flow chart providing details of the exemplary near-field-based technique of FIG. 13.

Referring to FIG. 15, the near-field concatenation-based emulation technique will now be described in greater detail wither reference to a specific technique for identifying concatenation points and for smoothing the resulting concatenated signal. Simultaneously, at steps 602 and 604, the concatenation-based emulation system inputs RA signals and RV signals. The RV signals may be sensed in using any of electrodes 32 or 34 (FIG. 3) in unipolar sensing mode. RA signals are sensed using leads 22 or 23 in unipolar sensing mode. At step 602 and 604, the RA and RV signals may be filtered using a high pass filter. Then, at step 606, the right ventricular channel signals are processed to detect the peaks of near-field R-waves and T-waves therein. In order to identify concatenation points for concatenating near-field portions of the atrial and ventricular channel signals, step 608 is then performed wherein the RV channel signals preceding the R-wave peak and following the T-wave peak are scanned to identify baseline points. That is, the RV channel signal is scanned within a pre-R-wave window and is also scanned within a post-T-wave window to identify points at which the RV channel signal crosses a baseline voltage, such as 0.0 V. In this regard, the technique described above with reference to FIG. 10 may be applied to the RV signals. Other techniques may be employed as well. Then portions of the RA channel signals occurring outside the pair of baseline points are extracted, at step 616. Simultaneously, portions of the RV channel signals occurring within the baseline points are extracted, at step 618. At step 620, the extracted portions of the RA and RV signals for the given heart beat are combined using the baseline points as concatenation points. At step 621, the relative polarities and the relative amplitudes of the signals may be adjusted to ensure that both P-waves and the R-waves and the same polarity and to ensue that the relative amplitudes of P-waves and R-waves are with a predetermined range. The concatenated signal is smoothed, at step 624, to eliminate any such discontinuities using any of the smoothing techniques discussed above.

Figure 16:
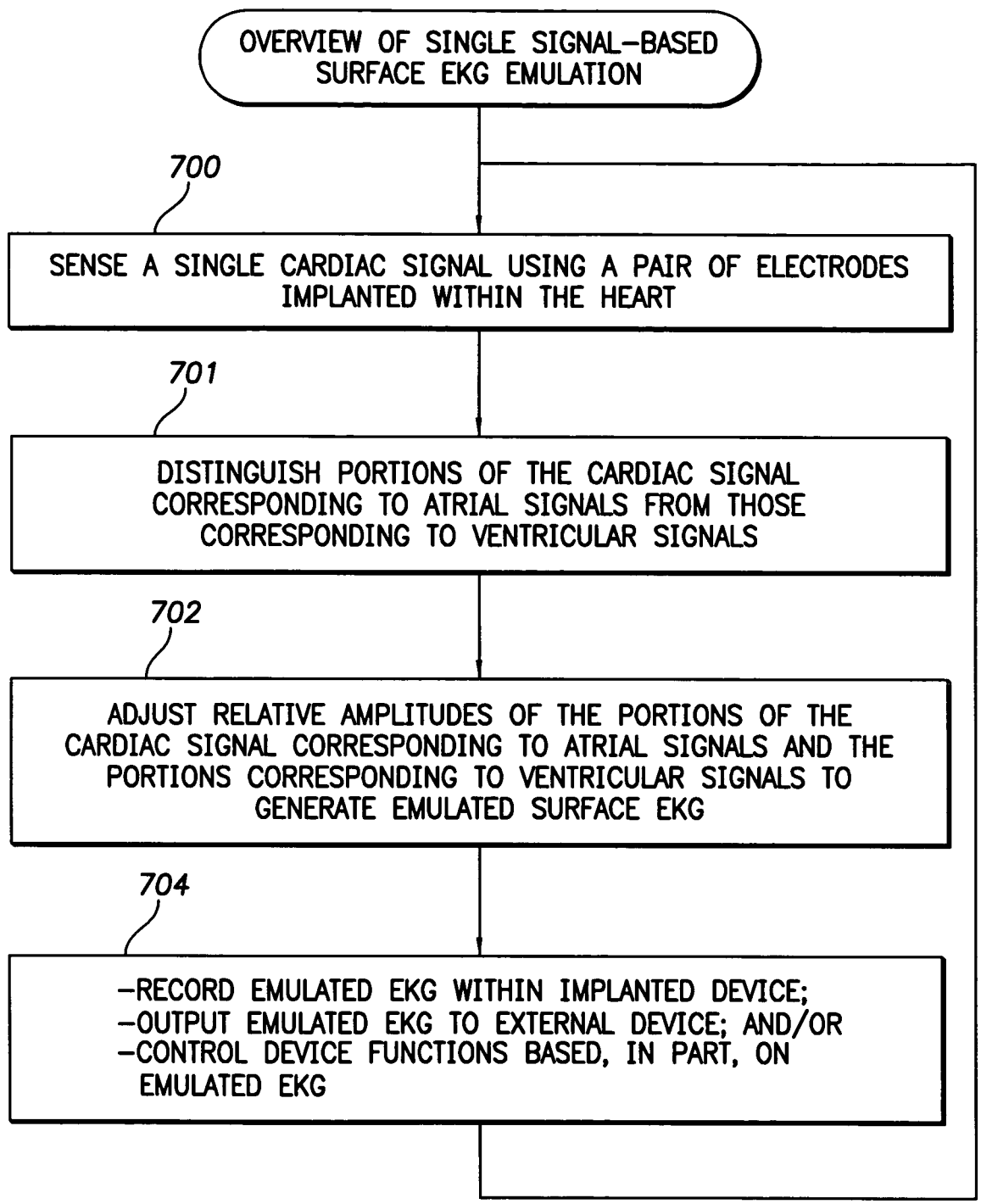
FIG. 16 is a flow chart providing an overview of an exemplary single signal-based technique for emulating a surface EKG for use either by the on-board surface EKG emulation system of FIG. 4 or the programmer-based surface EKG emulation system of FIG. 5.

Overview of Single Signal-Based Amplitude Adjustment Techniques for Emulating a Surface EKG FIG. 16 provides an overview of the amplitude adjustment-based technique wherein amplitudes of portions of a single internal cardiac signal are selectively adjusted to yield an emulated surface EKG. As with the concatenation-based techniques, the amplitude adjustment technique can be performed either by the on-board amplitude adjustment-based emulation system of the implanted device (system 103 of FIG. 4) or by the amplitude adjustment-based emulation controller of the external programmer (system 251 of FIG. 5). In the following, it will be assumed that the emulation is performed by the on-board system of the implanted device but the description is generally applicable to the programmer-based system of the external programmer. Briefly, at step 700, a cardiac signal is sensed using one or more electrodes implanted within the heart of the patient (such as an atrial unipolar signal sensed between atrial tip electrode 22 and the device case or a cross-chamber signal sensed between atrial tip electrode 22 and ventricular tip electrode 32.) Then, at step 701, the cardiac signal is analyzed to distinguish between signals generated in the atria and signals generated in the ventricles. At step 702, the amplitudes of the atrial and ventricular portions are selectively adjusted so as to emulate a surface EKG, typically by attenuating or amplifying one of the single portions relative to the other so as to achieve a preprogrammed ratio of average P-wave and R-wave peak amplitudes. As before, after the surface EKG has been emulated then, at step 704, the implanted device: records the emulated EKG within its internal memory; outputs the emulated EKG to an external programmer for display thereon; and/or controls certain functions of the implanted device based on the features of the emulated surface EKG.

Herein, two specific examples of single signal-based emulation are described. The first, based on an atrial unipolar signal, is described with reference to FIGS. 17-19. The second, based on a cross-chamber signal, is described with reference to FIGS. 20-22.

Emulation Based on Atrial Unipolar Signals

Figure 17:
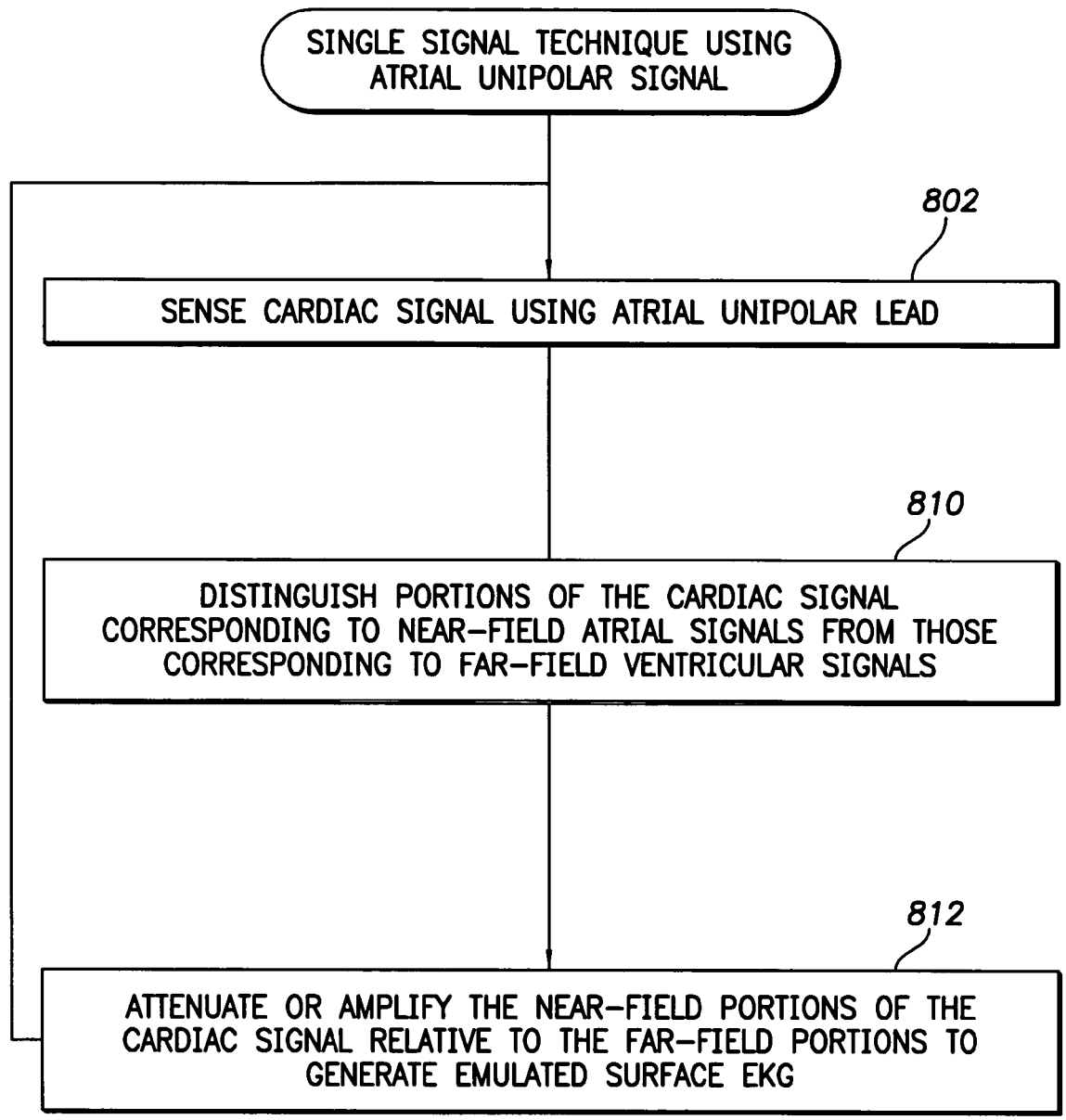
FIG. 17 is a flow chart summarizing an atrial unipolar-based technique, which is an example of the general single signal-based technique of FIG. 16.
Figure 18:
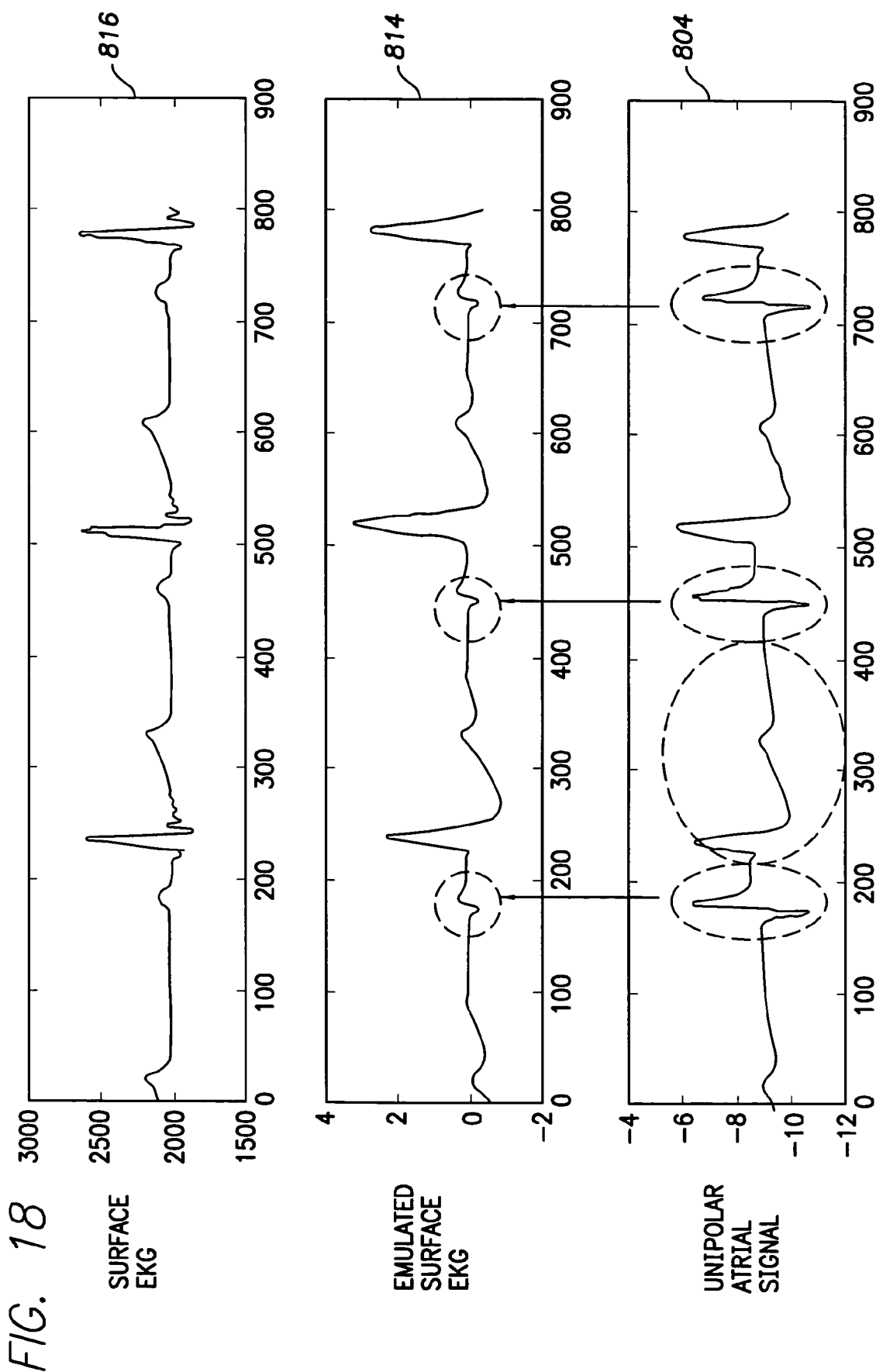
FIG. 18 is a diagram illustrating an atrial unipolar signal and an emulated surface EKG derived from the unipolar signal using the technique of FIG. 17.

The atrial unipolar-based technique is summarized in FIGS. 17-18. Briefly, the technique operates to emulate a surface EKG by attenuating near-field signals relative to far-field signals appearing within an atrial unipolar signal. At step 802 of FIG. 17, the implanted device senses an atrial unipolar signal. FIG. 18 illustrates an atrial unipolar IEGM signal 804. As can be seen, the atrial unipolar IEGM signals both include near-field and far-field signal portions. More specifically, atrial unipolar signal 804 includes a first portion 806 corresponding to near-field signals generated in the atria and a second portion 808 corresponding to far-field signals generated in the ventricles. The near-field signals are representative of local electrical activity in tissue near the atrial unipolar electrode; whereas the far-field signals are representative of the global electrical activity of the ventricles.

At step 810 of FIG. 17, the single signal-based emulation system analyzes the atrial unipolar signal to distinguish between the near-field and far-field portions. Then, at step 812, the device adjusts the amplitudes of the near-field signals 806 relative to the far-field signals 808 to yield an emulated surface EKG 814 (shown in FIG. 18.) In this example, the amplitudes of the near-field signals are attenuated by an amount sufficient so that the ratio of the P-wave to the R-wave is about 1:10. An actual surface EKG 816 is also provided in FIG. 18 for comparison. As can be seen, the emulated surface EKG provides a reasonably accurate approximation of the surface EKG, at least sufficient to allow easy identification of major features, such as P-waves, QRS complexes and T-waves. Unlike the concatenation techniques described above, the relative polarities of the near-field and far-field portions are typically not reversed since they are derived for the same signal and hence have the same polarity. Again, the relative amplitudes of the atrial and ventricular portions are adjusted to achieve a predetermined ratio of peak amplitudes, such as a ratio in the range of 1:4 or 1:10 of average P-wave peak amplitude to average R-wave peak amplitude. By selectively attenuating or amplifying near-field and far-field portions of an atrial unipolar signal, a reasonably accurate emulation of a surface EKG is thereby quickly and easily generated. Again, no sophisticated signal processing techniques are needed and no significant memory or computational resources are required. In any case, as shown in FIG. 16, after the surface EKG has been emulated then, the implanted device can record the emulated EKG within its internal memory, output the emulated EKG to an external programmer for display thereon and/or control certain functions of the implanted device including delivery of therapy.

Figure 19:
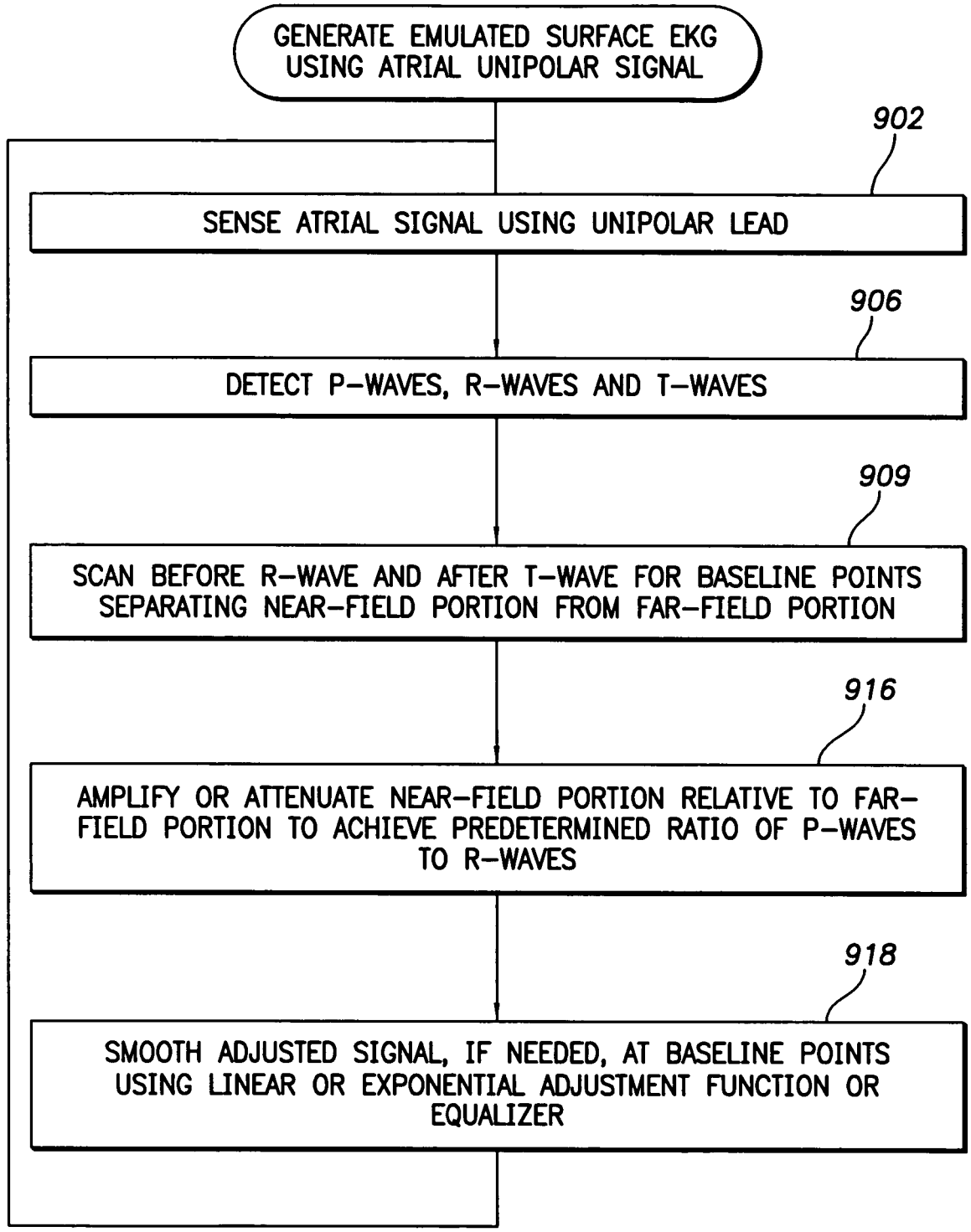
FIG. 19 is a flow chart providing details of the exemplary atrial unipolar-based technique of FIG. 17.

Referring to FIG. 19, the atrial unipolar amplitude adjustment technique will now be described in greater detail and, in particular, specific techniques for identifying the near-field and far-field portions and for smoothing the resulting signal will be described. Initially, at step 902, the single signal-based emulation system inputs an atrial unipolar signal. The atrial unipolar signal is sensed using leads 22 or 23. That is, voltage differences between either electrode 22 or 23 and the device case are sensed. In addition, at step 902, the atrial unipolar signal may be filtered in accordance with otherwise conventional techniques. Then, at step 906, the atrial unipolar signal is processed to detect the peaks of P-waves, R-waves and T-waves therein, using otherwise conventional event detection techniques. In order to distinguish between near-field and far-field portions of the atrial unipolar signal, step 909 is performed wherein signals preceding the R-wave peak and following the T-wave peak are scanned to identify baseline points. That is, the atrial unipolar signal is scanned within a pre-R-wave window and is also scanned within a post-T-wave window to identify points at which the signal crosses a baseline voltage, such as 0.0 V. Other techniques may be employed as well. Then portions of the atrial unipolar signal occurring outside the pair of baseline points (i.e. portions corresponding to the near-field signals) are attenuated or amplified, at step 916, relative to the portions occurring between the pair of baseline points so as to generate the emulated surface EKG. As noted, the attenuation or amplification is preferably performed to yield a predetermined ratio of average P-wave peak amplitude to average R-wave peak amplitude. Alternatively, of course, the far-field portion may be instead amplified or attenuated relative to the near-field portion.

The adjusted EKG signal is then smoothed, at step 918, if necessary to eliminate any discontinuities using any of the smoothing techniques discussed above. In this regard, if all portions of the near-field signals are amplified or attenuated by a fixed amount, then a discontinuity may occur at the baseline points. Other amplification or attenuation techniques may be employed that do not require subsequent smoothing. For example, the near-field portion may be multiplied by a smooth amplification or attenuation function that is zero at the baseline points but non-zero in the middle of the near-field section, so that the amplitude of the near-field portion at the baseline points is not affected whereas the P-wave is amplified or attenuated as needed. As can be appreciated, a wide range of techniques may be employed for use in amplifying or attenuating selected portions of the atrial unipolar signal so that smoothing is not required or for performing smoothing is circumstances where its is required and no attempt is made herein to itemize all possible techniques.

Emulation Based on Cross-Chamber Signals

Figure 20:
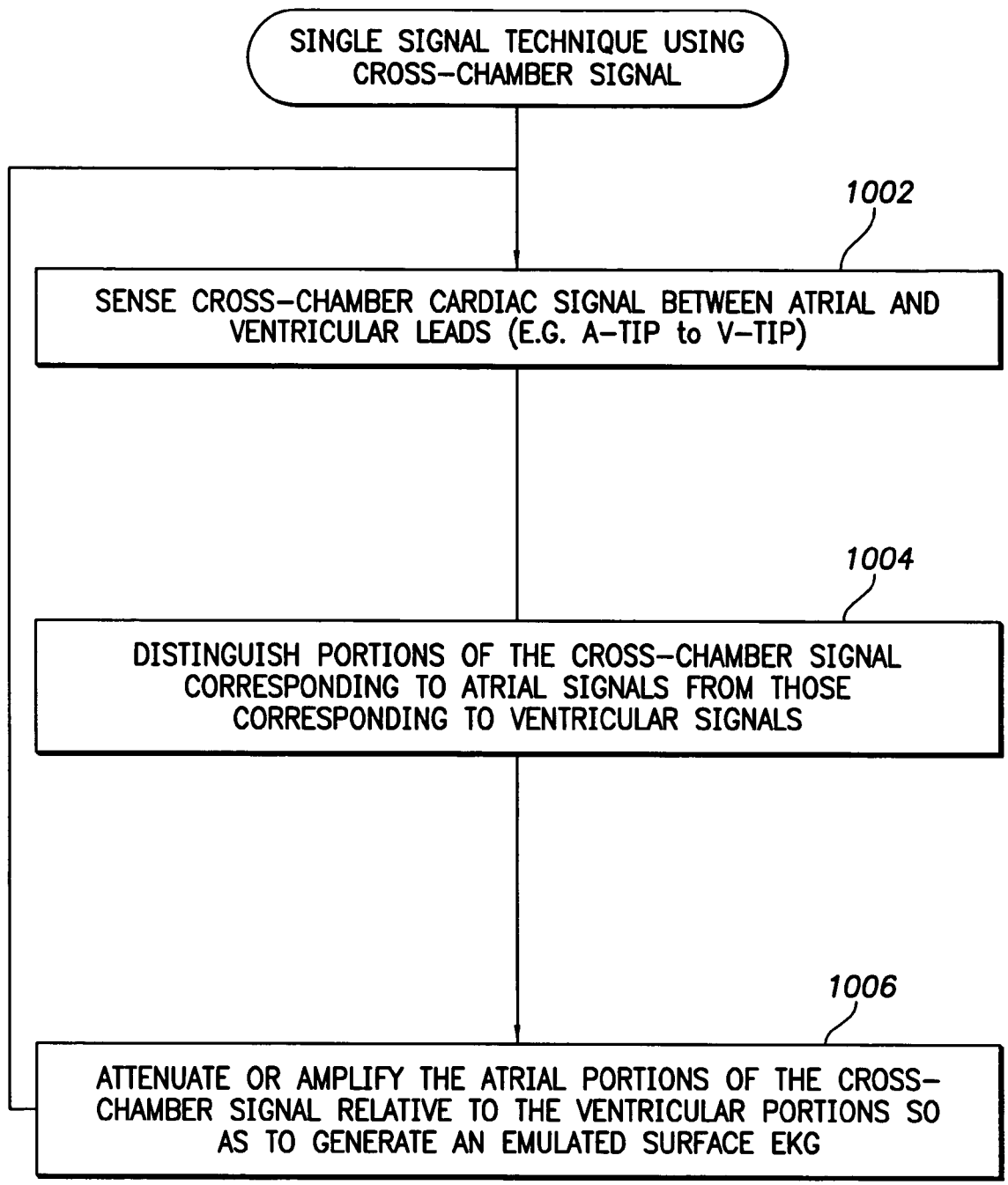
FIG. 20 is a flow chart summarizing a cross-chamber-based technique, which is another example of the general single signal-based technique of FIG. 16.
Figure 21:
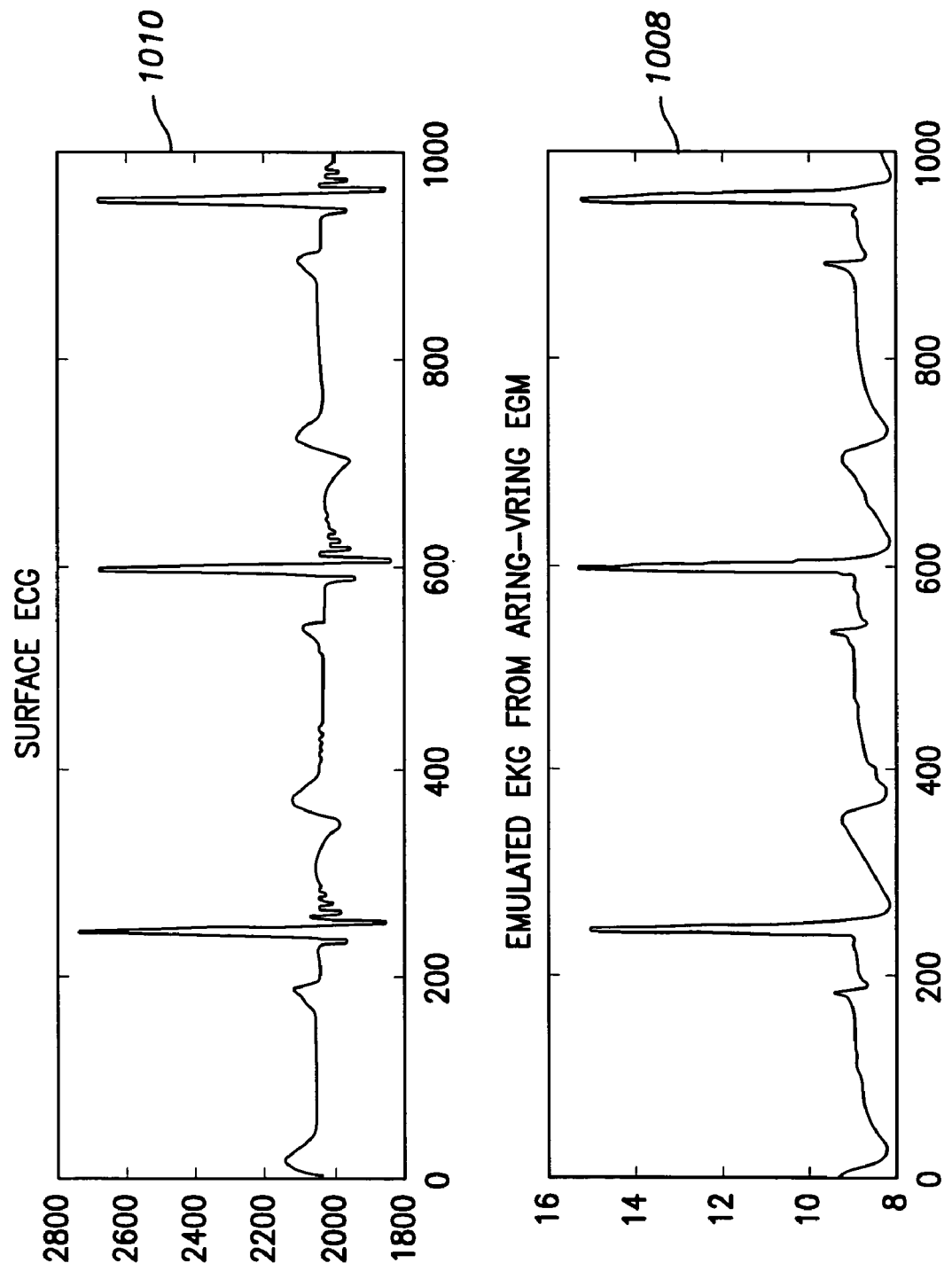
FIG. 21 is a diagram illustrating a cross-chamber signal (A-ring to V-ring) and an emulated surface EKG derived from the cross-chamber signal using the technique of FIG. 20.

The cross-chamber-based technique is summarized in FIGS. 20-21. Briefly, the technique operates to emulate a surface EKG by attenuating atrial signals relative to ventricular signals appearing within a cross-chamber signal sensed between at atrial electrode and a ventricular electrode, such as A-tip to V-tip. At step 1002 of FIG. 20, the implanted device senses a cross-chamber signal using a pair of leads—one in the atria and one in the ventricles. At step 1004, the single signal-based emulation system analyzes the cross-chamber signal to distinguish between atrial and ventricular portions. Then, at step 1006, the emulation system adjusts the amplitudes of the atrial signal portion relative to the ventricular signal portion to generate an emulated surface EKG 1008 (shown in FIG. 21.) In this example, the emulated EKG is derived from an A-ring to V-ring signal and the relative amplitudes of the atrial and ventricular portions are attenuated by an amount sufficient so that the ratio of the P-wave to the R-wave is about 1:10. An actual surface EKG 1010 is also provided in FIG. 21 for comparison. As can be seen, the emulated surface EKG provides an accurate approximation of the surface EKG. The relative amplitudes of the atrial and ventricular portions are adjusted to achieve a predetermined ratio of average P-wave peak amplitude to average R-wave peak amplitude. By selectively attenuating or amplifying atrial and ventricular portions of a cross-chamber signal, a reasonably accurate emulation of a surface EKG is thereby quickly and easily generated. Again, no sophisticated signal processing techniques are needed and no significant memory or computational resources are required. In any case, as shown in FIG. 16, after the surface EKG has been emulated then, the implanted device can record the emulated EKG within its internal memory, output the emulated EKG to an external programmer for display thereon and/or control certain functions of the implanted device including delivery of therapy.

Figure 22:
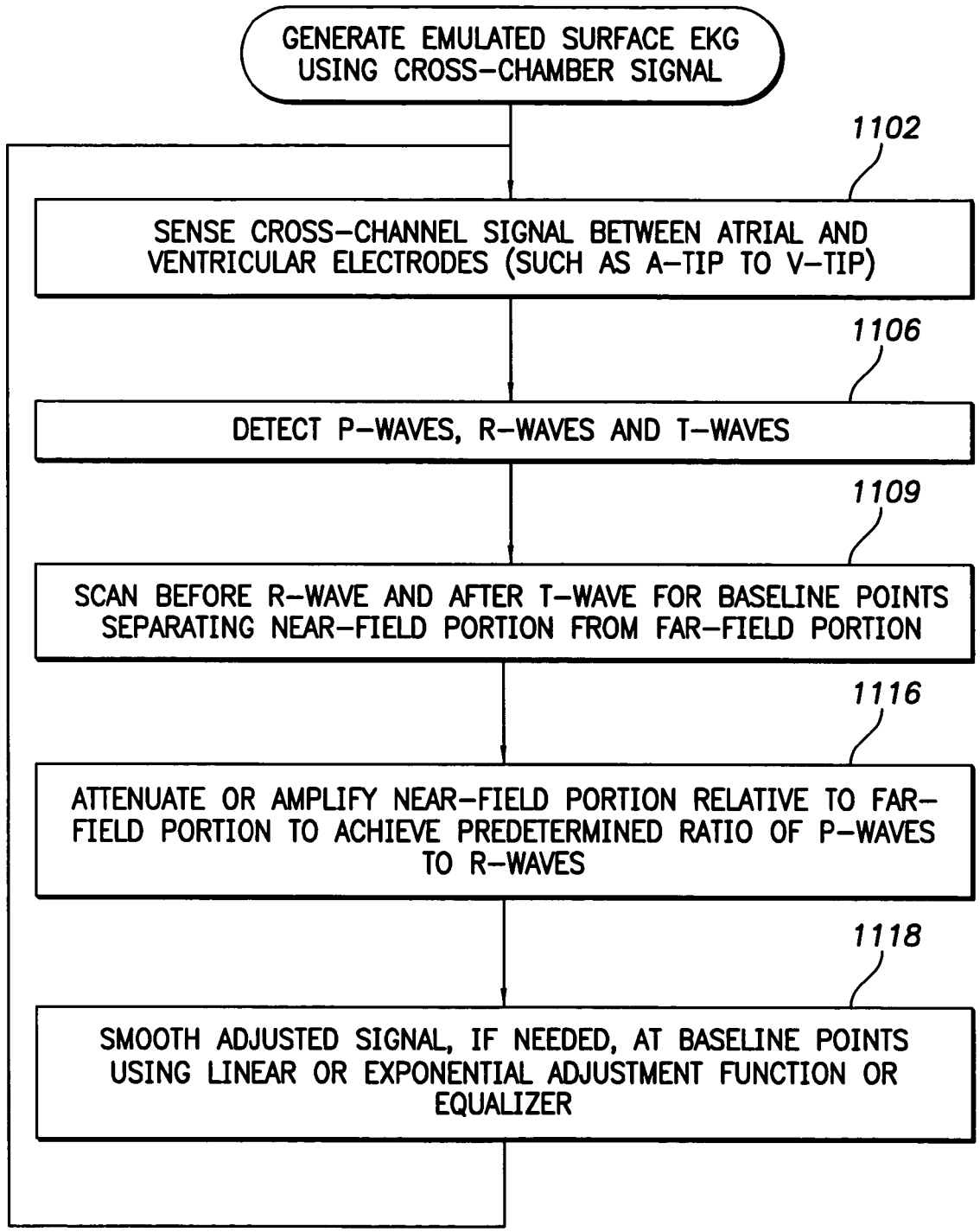
FIG. 22 is a flow chart providing details of the exemplary cross-chamber-based technique of FIG. 20.

Referring to FIG. 22, the cross-chamber amplitude adjustment technique will now be described in greater detail and, in particular, specific techniques for identifying the atrial and ventricular portions and for smoothing the resulting signal will be described. Initially, at step 1102, the single signal-based emulation system inputs a cross-chamber signal. The cross-chamber signal is sensed between an atrial electrode and a ventricular electrode such as between any of the following electrode pairs: A tip-V tip, A tip-V ring, A tip-RV Coil (i.e. the right ventricular coil electrode), A ring-V tip, A ring-V ring, A ring-RV Coil. If other electrodes are provided, other combinations may be employed. In addition, at step 1102, the cross-chamber signal may be filtered in accordance with otherwise conventional techniques. Then, at step 1106, the cross-chamber signal is processed to detect the peaks of P-waves, R-waves and T-waves therein, using otherwise conventional event detection techniques. In order to distinguish between atrial and ventricular portions of the cross-chamber signal, step 1109 is performed wherein signals preceding the R-wave peak and following the T-wave peak are scanned to identify baseline points at which the signal crosses a baseline voltage, such as 0.0 V. Again, other techniques may be employed as well. Then portions of the cross-chamber signal occurring outside the pair of baseline points (i.e. portions corresponding to the atrial signals) are attenuated or amplified, at step 1116, relative to the portions occurring between the pair of baseline points so as to generate the emulated surface EKG. The attenuation or amplification is preferably performed to yield a predetermined ratio of average P-wave peak amplitude to average R-wave peak amplitude. Alternatively, the ventricular portion may be instead amplified or attenuated relative to the near-field portion.

The adjusted EKG signal is then smoothed, at step 1118, if necessary to eliminate any discontinuities using any of the smoothing techniques discussed above.

Programmer/Implanted Device Interface

Referring to FIGS. 23 and 24, two separate techniques for generating an emulated surface EKG under the control of an external programmer will now be described. In the example of FIG. 23, the conversion of internal voltage signals to emulated surface EKG signals is performed by the implanted device under the control of the external programmer and the emulated signals are transmitted to the external programmer for display and further processing. In the example of FIG. 24, the conversion of internal signals into emulated EKG signals is performed by the external programmer using RA and RV channel signals transmitted from the implanted device. In both figures, steps performed by the external programmer are shown on the left whereas steps performed by the implanted device are shown on the right.

Referring first to FIG. 23, at step 1200, the external programmer, pursuant to commands entered by the physician or other trained medical personnel, transmits signals to the implanted device controlling the implanted device to emulate a surface EKG. At step 1202, the implanted device receives the control signals and begins to emulate surface EKG signals using internal electrical cardiac signals in accordance with either the multiple-single concatenation techniques of FIGS. 7-12 or the single signal techniques of FIGS. 13-22. At step 1204, the implanted device continuously transmits the emulated surface EKG signals to the external programmer. The surface EKG signals are received by the external programmer, at step 1206, and displayed for review by the physician, who can additionally control the external programmer to printout, store, or manipulate the emulated surface EKG as desired. At step 1208, again subject to control by the physician, the external programmer controls the implanted device to terminate emulation of the surface EKG. The termination control signals are received and processed by the implanted device at step 1210, which then deactivates the on-board surface EKG emulation system.

Referring to FIG. 24, the alternative technique wherein the external programmer performs the actual conversion of internal cardiac electrical signals into emulated surface EKG signals will now be briefly described. At step 1300, control signals are transmitted from the external programmer to the implanted device, which, at step 1302, responds by sensing RA and RV channel signals. The signals are transmitted continuously from the implanted device to the external programmer beginning at step 1304. The external programmer receives the RA and RV channel signals, at step 1306, and, using any of the techniques described, generates the emulated surface EKG signals. At step 1308, the surface EKG is displayed. Eventually, under the control of the physician, the surface EKG emulation is terminated at steps 1310 and 1312.

Although not shown in FIGS. 23 and 24, in the alternative, the implanted device may be configured to emulate the surface EKG at all times and to record the EKG in internal memory (in a circular buffer) for subsequent transmission to the external programmer. Also, rather than using an external programmer to review the emulated surface EKG, other external devices may alternatively be employed, such as dedicated EKG display devices, bedside monitors, etc.

What have been described are various techniques for generating an emulated surface EKG. In general, the embodiments described herein are merely illustrative and should not be construed as limiting the scope of the invention, which is to be interpreted in accordance with the claims that follow.

What is claimed is:

1. A method for emulating a surface electrocardiogram (EKG) of a patient in which an implantable cardiac stimulation device is implanted, the method comprising:
    sensing first and second cardiac signals using electrodes implanted within the patient;
    identifying a pair of baseline points in each the first and second cardiac signals; and
    selectively concatenating that portion of the first cardiac signal that lies between the pair of baseline points with that portion of the second cardiac signal that lies outside the pair of baseline points, using the baseline points as concatenation points to yield an emulated surface EKG.

2. The method of claim 1 wherein sensing cardiac signals comprises:
    sensing atrial signals using at least one atrial electrode; and
    sensing ventricular signals using at least one ventricular electrode.

3. The method of claim 1 wherein sensing cardiac signals using electrodes implanted within the patient comprises:
    sensing atrial signals using unipolar sensing by employing an atrial electrode in combination with a housing of the device; and
    sensing ventricular signals using unipolar sensing by employing a ventricular electrode in combination with a housing of the device.

4. The method of claim 3 wherein the atrial electrode is a right atrial tip electrode, a right atrial ring electrode, an SVC coil electrode, a left atrial ring electrode, a left atrial coil electrode or a transseptal atrial electrode and wherein the ventricular electrode is a right ventricular tip electrode, a right ventricular ring electrode or a right ventricular coil electrode, a left ventricular tip electrode, a left ventricular ring or a ventricular epicardial electrode.

5. The method of claim 1 wherein selectively concatenating portions of the cardiac signals further comprises:
    smoothing the emulated surface EKG at concatenation points.

6. The method of claim 1 wherein selectively concatenating portions of the cardiac signals further comprises:
    aligning signal polarities of the concatenated portions.

7. The method of claim 1 further comprising controlling device functions based, in part, on the emulated surface EKG.

8. The method of claim 1 performed entirely by the implantable medical device.

9. The method of claim 1 performed by the implantable medical device in combination with a device external to the patient, and further comprising transmitting the separate cardiac signals to the external device and wherein selectively concatenating portions of the cardiac signals to yield an emulated surface EKG is performed by the external device.

10. A system for emulating a surface electrocardiogram (EKG) of a patient, the system comprising:
    one or more electrodes implanted within the patient;

sensing circuitry operative to sense first and second cardiac signals using the one or more electrodes; and an EKG emulation unit operative to identify a pair of baseline points in each of the first and second cardiac signals and to selectively concatenate that portion of the first cardiac signal that lies between the pair of baseline points with that portion of the second cardiac signal that lies outside the pair of baseline points, using the baseline points as concatenation points to yield an emulated surface EKG.

* * * * *